US006632652B1

(12) United States Patent
Austin et al.

(10) Patent No.: US 6,632,652 B1
(45) Date of Patent: Oct. 14, 2003

(54) REVERSIBLY SEALABLE MICROSTRUCTURE SORTING DEVICES

(75) Inventors: Robert H. Austin, Princeton, NJ (US); Robert H. Carlson, Union City, CA (US)

(73) Assignee: Princeton University, Princeton, NJ (US)

( * ) Notice: Subject to any disclaimer, the term of this patent is extended or adjusted under 35 U.S.C. 154(b) by 0 days.

(21) Appl. No.: 09/153,054

(22) Filed: Sep. 15, 1998

Related U.S. Application Data

(63) Continuation-in-part of application No. PCT/US97/15063, filed on Aug. 26, 1997.
(60) Provisional application No. 60/024,589, filed on Aug. 26, 1996.

(51) Int. Cl.[7] .................................................. C12M 1/00
(52) U.S. Cl. .............................. 435/287.2; 435/283.1; 435/7.1; 204/450; 204/600; 204/180.1; 204/299; 204/127.1; 209/155; 209/156; 422/55; 422/57; 436/527; 436/164; 436/149
(58) Field of Search ........................... 435/287.2, 283.1, 435/7.1; 204/450, 600, 180.1, 299, 127.1; 209/155, 156; 436/527, 164, 149, 807; 422/55, 57

(56) References Cited

U.S. PATENT DOCUMENTS

| | | |
|---|---|---|
| 3,799,742 A | 3/1974 | Coleman |
| 3,906,929 A | 9/1975 | Augspurger |
| 4,233,029 A | 11/1980 | Columbus |
| 4,302,313 A | 11/1981 | Columbus |
| 4,350,768 A | 9/1982 | Tihon et al. |
| 4,561,157 A | 12/1985 | Lowe et al. |
| 4,618,476 A | 10/1986 | Columbus |
| 4,676,274 A | 6/1987 | Brown |
| 4,790,640 A | 12/1988 | Nason |
| 4,886,761 A | 12/1989 | Gustafson et al. |
| 4,906,439 A | 3/1990 | Grenner |
| 4,908,112 A | 3/1990 | Pace |
| 4,911,782 A | 3/1990 | Brown |
| 4,963,498 A | 10/1990 | Hillman et al. |
| 5,976,826 A | 11/1990 | Singhvi et al. ................ 435/29 |
| 4,999,283 A | 3/1991 | Zavos et al. |
| 5,114,858 A | 5/1992 | Williams et al. |
| 5,135,720 A | 8/1992 | Uchida |
| 5,147,606 A | 9/1992 | Charlton et al. |
| 5,188,963 A | 2/1993 | Stapleton |

(List continued on next page.)

FOREIGN PATENT DOCUMENTS

| | | | |
|---|---|---|---|
| GB | 2238619 | 6/1991 | |
| GB | 2239311 | 6/1991 | |
| JP | 4152885 | 5/1992 | |
| WO | WO 91/11262 | 8/1991 | |
| WO | WO 91/13338 | 9/1991 | |
| WO | WO 97/33737 | 9/1997 | ........... B29C/37/00 |
| WO | WO 99/54786 | 10/1999 | ............. G03F/7/00 |
| WO | WO 99/61888 | 12/1999 | ........... G01N/15/14 |

OTHER PUBLICATIONS

Abstract of Jaanese Patent No. 4,152,885 dated May 26, 1992.

(List continued on next page.)

*Primary Examiner*—Kenneth R. Horlick
*Assistant Examiner*—Janell E. Taylor
(74) *Attorney, Agent, or Firm*—Miles & Stockbridge P.C.

(57) ABSTRACT

Methods and apparatus for sorting microstructures, such as macromolecules, viruses, cells, and minute particles, in a fluid using microlithographic sorting array that is reversibly sealed by a cover. A silicone elastomer cover is used in one embodiment. In another, silicon microstructures are used to case elastomeric replicas of obstacle arrays, the tops of which reversibly seal against a flat surface. The reversible seal allows access to fractionated microstructures within the structure for further analysis.

60 Claims, 17 Drawing Sheets

U.S. PATENT DOCUMENTS

| | | | |
|---|---|---|---|
| 5,278,048 A | | 1/1994 | Parce et al. |
| 5,296,375 A | | 3/1994 | Kricka et al. |
| 5,304,487 A | | 4/1994 | Wilding et al. |
| 5,427,663 A | * | 6/1995 | Austin et al. ............ 204/180.1 |
| 5,427,946 A | | 6/1995 | Kricka et al. |
| 5,486,335 A | | 1/1996 | Wilding et al. |
| 5,498,392 A | | 3/1996 | Wilding et al. |
| 5,512,131 A | | 4/1996 | Kumar et al. ............ 156/655.1 |
| 5,549,796 A | | 8/1996 | Chu et al. |
| 5,567,302 A | | 10/1996 | Song |
| 5,637,458 A | * | 6/1997 | Frankel et al. ................. 435/6 |
| 5,707,799 A | | 1/1998 | Hansmann et al. ............ 435/6 |
| 5,776,748 A | | 7/1998 | Singhvi et al. ............. 435/180 |
| 5,837,115 A | * | 11/1998 | Austin et al. ............... 204/450 |

OTHER PUBLICATIONS

Abstract of Great Britain Patent No. 2,239,311 dated Jun. 26, 1991.

"Micromechanics Imitate Blood Vessels" Design News 15 (Mar. 22, 1993).

Mark Ivker, "Direct Observation of Reptation in Artificial Gel Environments" (Spring, 1991) (Bachelor of Arts thesis, Princeton University).

George Wallis et al., "Field Assisted Glass–Metal Sealing," 40 J. Applied Physics 3946–49 (Sep., 1969).

Masao Washizu, et al., "Handling Biological Cells Utilizing a Fluid Integrated Circuit," IEEE Industry Applications Society Annual Meeting Presentations 1735–40 (Oct. 2–7, 1988).

Masao Washizu, et al., "Handling Biological Cells Utilizing a Fluid Integrated Circuit," 26 IEEE Transactions on Industry Applications 352–357 (1990).

W. Volkmuth et al., "Observation of Electrophoresis of Single DNA Molecules in Nanofabricated Arrays," presentation at joint annual meeting of Biophysical Society and the American Society for Biochemistry and Molecular Biology (Feb. 9–13, 1992).

W.D. Volkmuth et al., "DNA Electrophoresis in Microlithographic Arrays," 356 Nature 600–02 (Aug. 13, 1992).

Anderson, Janelle R., et al., "Fabrication of Topologically Complex Three–Dimensional Microfluidic Systems in PDMS by Rapid Prototyping," 72(14) Analytical Chemistry 3158–64 (Jul. 15, 2000).

Bousse, Luc, et al., "Electrokinetically Controlled Microfluidic Analysis Systems," 29 Annu. Rev. Biophys. Biomol. Struct. 155–81 (2000).

Carlson, Robert H., et al., "Self–Sorting of White Blood Cells in a Lattice," 79(11) Physical Review Letters 2149–53 (Sep. 15, 1997).

Chou, Hou–Pu, et al., "A Microfabricated Device for Sizing and Sorting DNA Molecules," 96 Proc. Natl. Acad. Sci. USA 11–13 (Jan. 1999).

Chou, Hou–Pu, et al., "Disposable Microdevices for DNA Analysis and Cell Sorting," in Proceedings of the Solid–State Sensor and Actuator Workshop, Hilton Head, S.C. 11–14 (Jun. 8–11, 1998).

Chou, Hou–Pu, et al., "Integrated Elastomer Fluidic Lab–on–a–chip–Surface Patterning and DNA Diagnostics," Solid State Actuator and Sensor Workshop, Hilton Head, S.C., Cleveland Heights, Ohio: Transducers Research Foundation, Inc., 4 pages (Jun. 4–8, 2000).

Delamarche, Emmanuel, et al., "Patterned Delivery of Immunoglobulins to Surfaces Using Microfluidic Networks," 276 Science 779–81 (May 2, 1997).

Duffy, David C., et al., "Rapid Prototyping of Microfluidic Switches in Poly(Dimethyl Siloxane) and Their Actuation by Electro–Osmotic Flow," 9 J. Micromech. Microeng. 211–217 (Apr. 1, 1999).

Effenhauser, Carlo S., et al., "Integrated Capillary Electrophoresis on Flexible Silicone Microdevices: Analysis of DNA Restriction Fragments and Detection of Single DNA Molecules on Microchips," 69(17) Anal. Chem. 3451–57 (Sep. 1, 1997).

Fu, Anne Y., et al., "A Microfabricated Fluorescence–Activated Cell Sorter," 17 Nature Biotechnology 1109–1111 (Nov. 1999).

Hosokawa, Kazuo, et al., Handling of Picoliter Liquid Samples in a Poly (Dimethylsiloxane)–Based Microfluidic Device, 71(20) Anal. Chem. 4781–85 (Oct. 15, 1999).

Jackman, Rebecca J., et al., "Design and Fabrication of Topologically Complex, Three–Dimensional Microstructures," 280 Science 2089–91 (Jun. 26, 1998).

Jackman, Rebecca J., et al., "Fabrication of Submicrometer Features on Curved Substrates by Microcontract Printing," 269 Science 664–65 (Aug. 4, 1995).

Kane, Ravi S., et al., "Patterning Proteins and Cells Using Soft Lighography," 20(23–24) Biomaterials 2363–76 (1999).

Quake, Stephen R., et al., "From Micro–to Nanofabrication with Soft Materials," 290 Science 1536–40 (Nov. 24, 2000).

Quake, Stephen R., et al., "The Dynamics of Partially Extended Single Molecules of DNA," 388 Nature 151–54 (Jul. 10, 1997).

Rogers, John A., et al., "Constructing Single–and Multiple–Helical Microcoils and Characterizing Their Performance as Components of Microinductors and Microelectromagnets," 6(3) Journal of Microelectromechanical Systems, 184–92 (Sep. 1997).

Unger Marc A., et al., "Monolithic Microfabricated Valves and Pumps by Multilayer Soft Lithography," 288 Science 113–16 (Apr. 7, 2000).

Washizu, Masao, "Manipulation of Biological Objects in Micromachined Structures," IEEE Micro Electro Mechanical Systems 196–201 (Feb. 4, 1992).

Xia, Younan, et al., "Complex Optical Surfaces Formed by Replica Molding Against Elastomeric Masters," 273 Science 347–49 (Jul. 19, 1996).

Xia, Younan, et al., "Soft Lithography," 37 Angew. Chem. Int. Ed. 551–75 (*circa* Mar. 1998).

Yang, Peidong, et al., "Mirrorless Lasing from Mesostructured Waveguides Patterned by Soft Lithography," 287 Science 465–67 (Jan. 21, 2000).

Zhao, Xiao–Mei, et al., "Fabrication of Single–Mode Polymeric Waveguides Using Micromolding in Capillaries," 8(5): Adv. Mater. 420–24 (*circa* Apr. 1996).

* cited by examiner

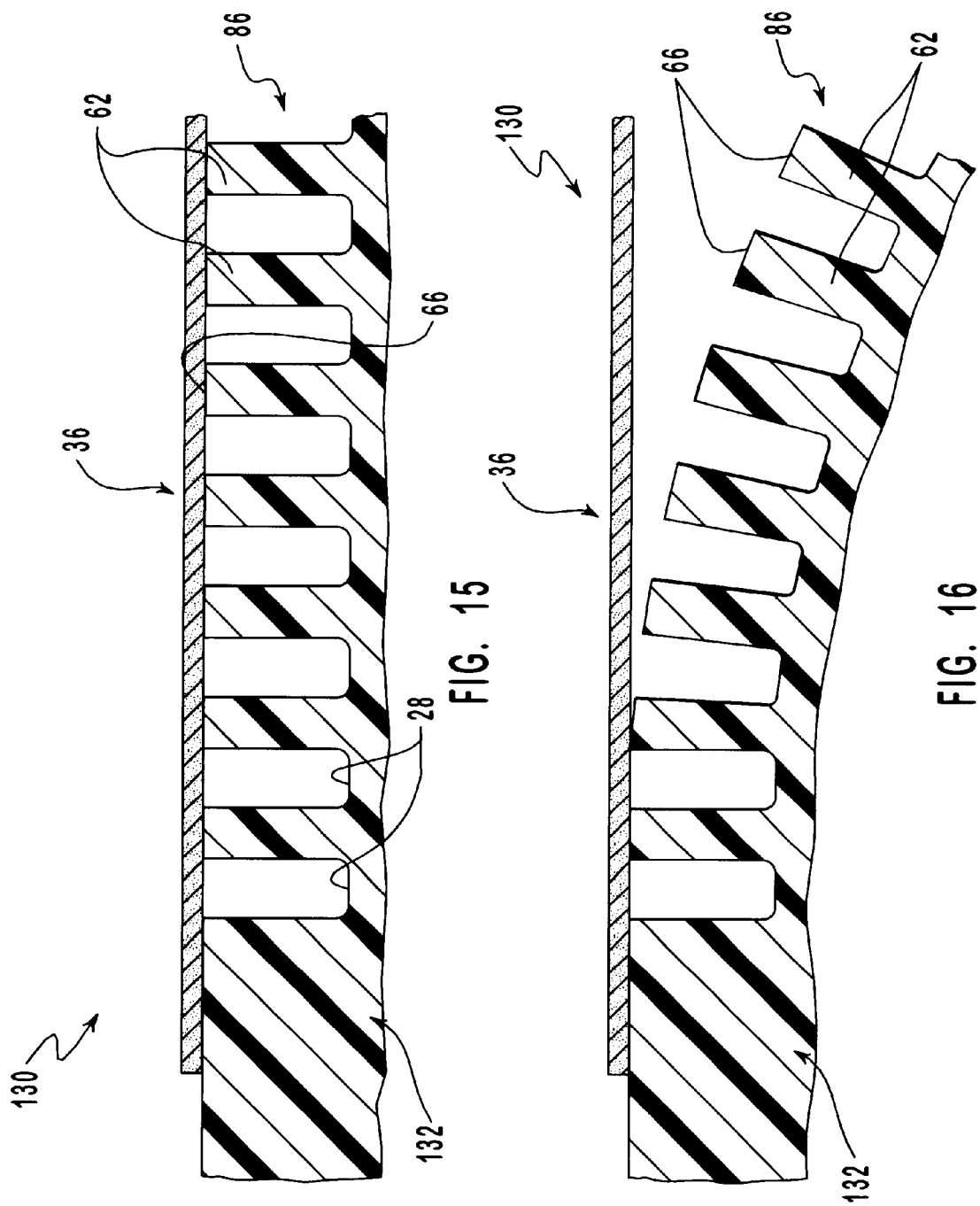

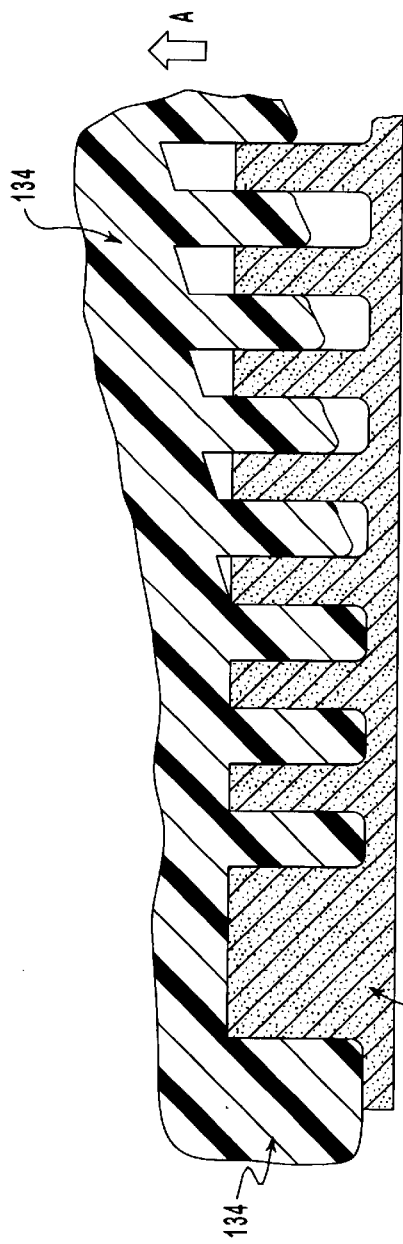
FIG. 17C
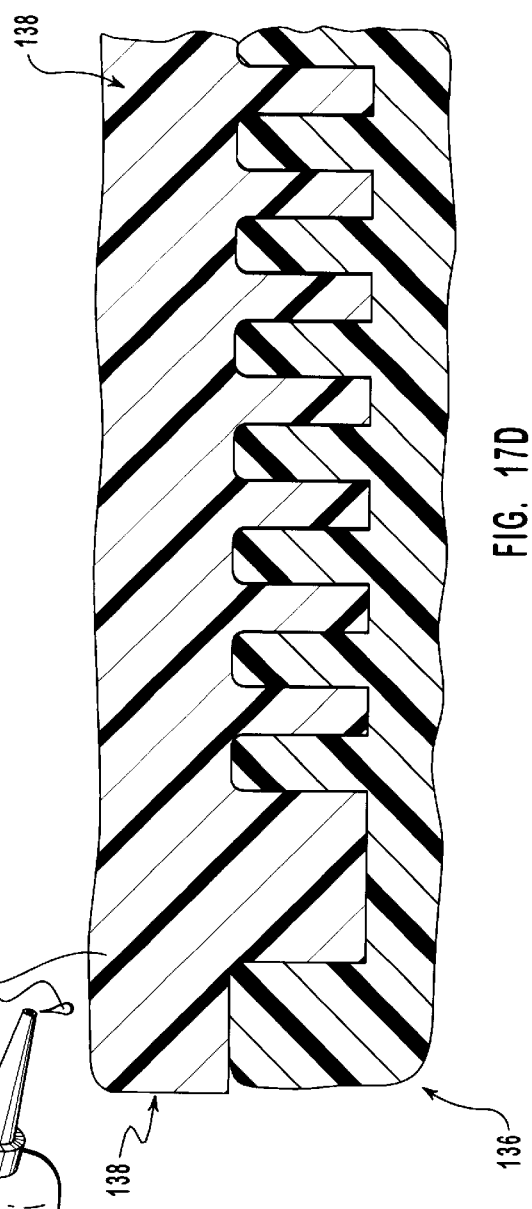
FIG. 17D
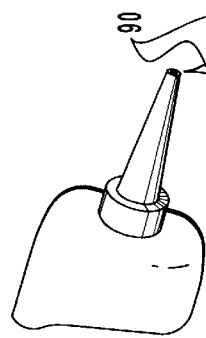

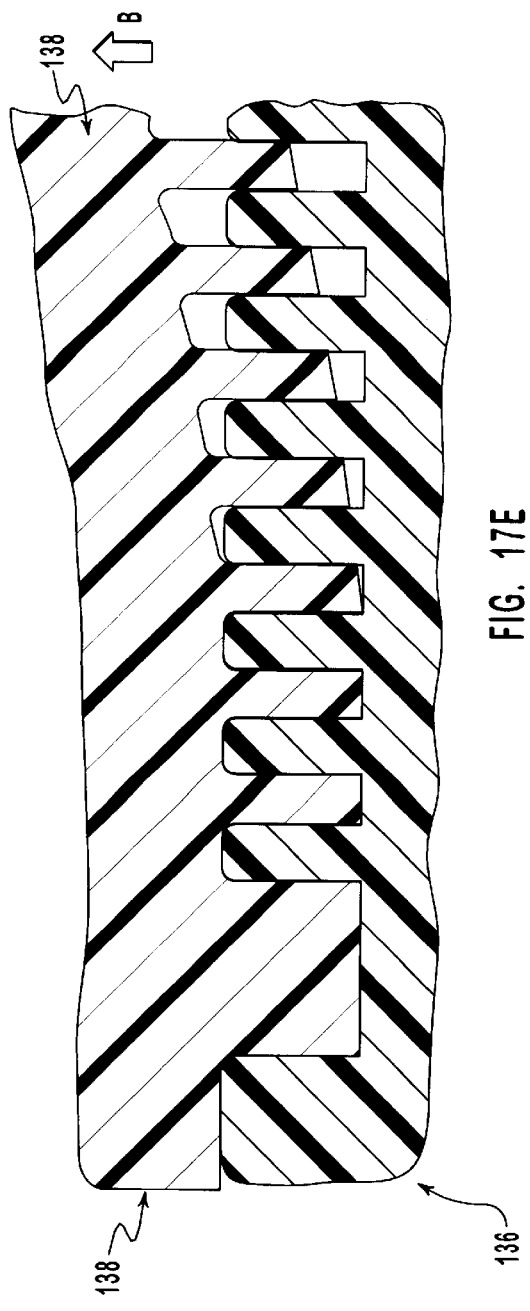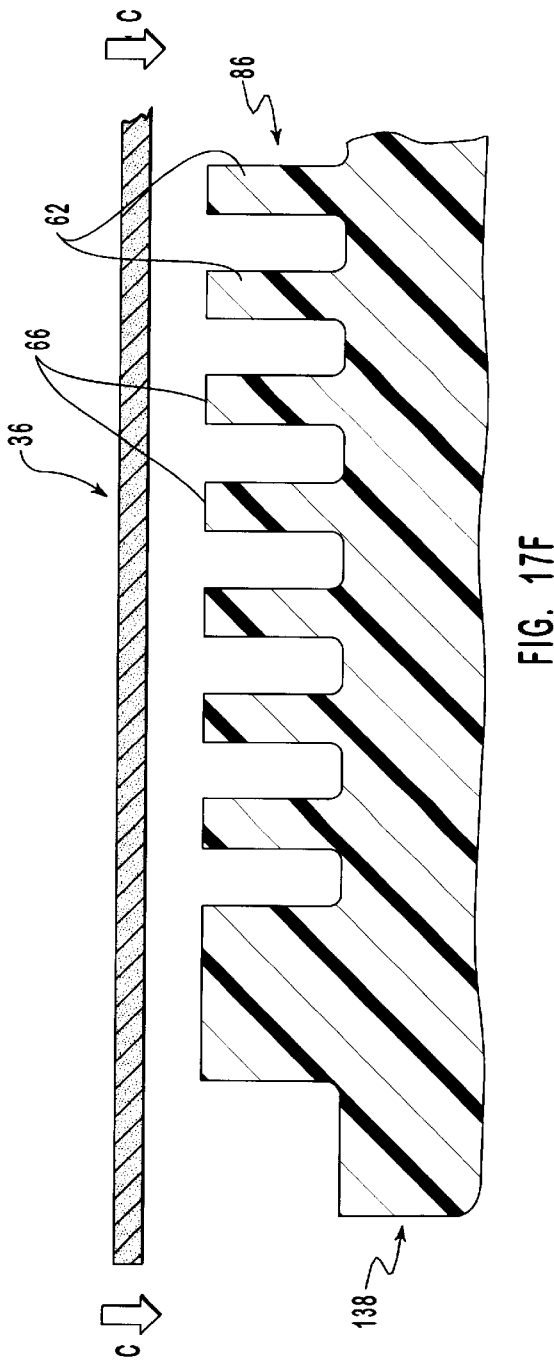
FIG. 17E
FIG. 17F

REVERSIBLY SEALABLE MICROSTRUCTURE SORTING DEVICES

RELATED APPLICATIONS

This application is a continuation-in-part application of International Patent Application Serial No. PCT/US97/15063 that was filed on Aug. 26, 1997 (hereinafter "the International Application"). The International Application designates the United States and claims priority under 35 U.S.C. § 119(e) to U.S. Provisional Patent Application Serial No. 24,589 that was filed on Aug. 26, 1996.

BACKGROUND

1. The Field of the Invention

The invention relates to apparatus and methods for fractionating microstructures such as free cells, viruses, macromolecules, or minute particles. More particularly, the present invention relates to apparatus and methods for sorting such microstructures in suspension in a fluid medium, and if desired, for simultaneously viewing individual of those microstructures during the process.

2. Background Art

The sizing, separation, and study of microstructures such as free cells, viruses, macromolecules, and minute particles, are important tools in molecular biology. For example, this fractionation process when applied to DNA molecules is useful in the study of genes and ultimately in planning and the implementation of genetic engineering processes. The fractionation of larger microstructures, such as mammalian cells, promises to afford cell biologists new insight into the functioning of these basic building blocks of living creatures. One method for estimating the size of small DNA molecules is the process of gel electrophoresis.

In gel electrophoresis an agarose gel is spread in a thin layer and allowed to harden into a firm composition. The composition comprises a fine network of fibers retaining therewithin a liquid medium, such as water. The fibers of the agarose gel cross and interact with each other to form a lattice of pores through which molecules smaller than the pores may migrate in the liquid retained in the composition. The size of the pores in the lattice is determined generally by the concentration of the gel used.

Slots are cast in one end of the gel after the gel is hardened, and DNA molecules are placed into the slots. A weak electric field of typically 1–10 volts per centimeter is then generated in the gel by placing the positive pole of an electric power source in one end of the gel and the negative pole of the power source in the opposite end.

In a free solution, the mobility of a DNA molecule is independent of the length of the molecule or of the size of the applied electric field. In a hindered environment, however, aside from the structure of the hindered environment, the mobility of a molecule becomes a function of the length of the molecule and the intensity of the electric field.

The gels used in gel electrophoresis is just such a hindered environment. Molecules are hindered in their migration through the liquid medium in the gel by the lattice structure formed of the fibers in the gel. The molecules nevertheless when inducted by the electric field, move through the gel by migrating through the pores of the lattice structure. Smaller molecules are able to pass through the pores more easily and thus more quickly than are larger molecules. Thus, smaller molecules advance a greater distance through the gel composition in a given amount of time than do larger molecules. The smaller molecules thereby become separated from the larger molecules in the process. In this manner DNA fractionation occurs.

The process has several inherent limitations, however. For example, the pore size in the lattice of gels cannot be accurately measured or depicted. Therefore, the lengths of the molecules migrating through the lattice cannot be accurately measured. It has also been found that DNA molecules larger than 20 megabasepairs in length cannot be accurately fractionated in gels. Apparently, the pore size in the lattice of such materials cannot be increased to permit the fractionation of larger molecules, much less even larger particles, viruses, or free cells.

Further, the lattice structure formed when a gel hardens is not predictable. It is not possible to predict the configuration into which the lattice structure will form or how the pores therein will be positioned, sized, or shaped. The resulting lattice structure is different each time the process is carried out. Therefore, controls and the critical scientific criteria of repeatability cannot be established.

Gel electrophoresis experiments cannot be exactly duplicated in order to predictably repeat previous data. Even if the exact lattice structures formed in one experiment were determinable, the structure could still not be reproduced. Each experiment is different, and the scientific method is seriously slowed.

Also, the lattice structure of a gel is limited to whatever the gel will naturally produce. The general size of the pores can be dictated to a degree by varying the concentration of the gel, but the positioning of the pores and the overall lattice structure cannot be determined or designed. Distinctive lattice structures tailored to specific purposes cannot be created in a gel.

Further, because the lattice structure arrived at depends upon the conditions under which hardening of the gel occurs, the lattice structure even in a single composition need not be uniform throughout.

Another shortcoming of gel electrophoresis is caused by the fact that a gel can only be disposed in a layer that is relatively thick compared to the pores in its lattice structure, or correspondingly to the size of the DNA molecules to be fractionated. Thus, the DNA molecules pass through a gel in several superimposed and intertwined layers. Individual DNA molecules cannot be observed separately from the entire group. Even the most thinly spread gel is too thick to allow an individual DNA molecule moving through the gel to be spatially tracked or isolated from the group of DNA molecules.

The diffusion of long polymers in complex environments where the mobility of the polymer is greatly perturbed is both a challenging statistical physics problem and a problem of great importance in the biological sciences. The length fractionation of charged polymers, such as DNA in gels, is a primary tool of molecular biology. One of the main stumbling blocks to understanding quantitatively the physical principles behind the length-dependent mobility of long polymers in complex environments has, however, been the ill-characterized nature of the hindering environment, the gel.

A known sorting apparatus 20 is illustrated in FIG. 1. Sorting apparatus 20 has utility in fractionating and optionally for simultaneously viewing microstructures, such as free cells, macromolecules, and minute particles in a fluid medium, and doing so as desired in essentially a single layer. Sorting apparatus 20 is comprised of a substrate 22 having a shallow receptacle 24 located on a side 26 thereof. In the embodiment shown, receptacle 24 is recessed in side 26 of substrate 22, although other structures for producing a recess such as receptacle 24 would be workable in the context of the present invention.

Receptacle 24 includes a floor 28 shown to better advantage in FIG. 2 as being bounded by a pair of upstanding opposing side walls 30, 31 and a first end 32 and a second end 34. The height of side walls 30, 31 define a depth of receptacle 24. The depth of receptacle 24 is commensurate with the size of the microstructures to be sorted in sorting apparatus 20. The depth of receptacle 24 is specifically tailored to cause those microstructures in a fluid medium in receptacle 24 to form essentially a single layer. Thus, when the microstructures are caused to migrate in the fluid medium through receptacle 24, the microstructures do so in essentially the single layer. The migration of the microstructures occurs in a migration direction indicated by arrow M defined relative to sorting apparatus 20.

Substrate 22 may be comprised of any type material which can be photolithographically processed. Silicon is preferred, however other materials, such as quartz and sapphire can also be used.

In accordance with one aspect of a known sorting apparatus, such as sorting apparatus 20, capping means are provided for covering receptacle 24 intermediate first end 32 and second end 34 thereof and for affording visual observation of the migration of the microstructures within receptacle 24. As shown by way of example in FIG. 1, a coverslip 36 extends across receptacle 24 in substrate 22 from one of the pair of upstanding opposing side walls 30 to the other of said pair of upstanding opposing side walls 31. The manner by which coverslip 36 is bonded to side 26 of substrate 22 and to the structures therebetween will be discussed in detail subsequently.

According to another aspect of a known sorting apparatus, such as sorting apparatus 20, means are positioned within receptacle 24 for interacting with the microstructures to partially hinder the migration of the microstructures in the migration direction.

As is suggested in the exploded view of FIG. 2, one form of such a means is an array 38 of minute obstacles 39 upstanding from floor 28 of receptacle 24. Obstacles 39 are sized and sized as to advance the particular sorting objective of sorting apparatus 20. The manner of forming obstacles 39 of array 38, as well as another example of another embodiment of obstacles utilizable in such an array, will be discussed in substantial detail below.

Coverslip 36 is so secured to the top of obstacles 39 in array 38 as to preclude migration of microstructures between the obstacles 39 and coverslip 36. Coverslip 36 is optionally transparent, so as to permit visual observation therethrough of the migration of microstructures through array 38. Coverslip 36 may be comprised of any ceramic material. Pyrex is preferred, but other materials, such as quartz and sapphire, for example, may also be used.

In accordance with another aspect of a known sorting apparatus, such as sorting apparatus 20, electric force means is provided for generating an electric field in the fluid medium in receptacle 24. The electric field induces the microstructures to migrate through the fluid medium, either from first end 32 to second end 34 or from second end 34 to first end 32, depending upon the polarity of the electric field and whether the microstructures are positively or negatively charged. Negatively charged microstructures, such as DNA molecules, will be induced to flow toward the positive pole. Positively charged microstructures, such as proteins, will be induced to flow toward the negative pole.

By way of example, a first electrode 40 is shown in FIG. 2 as being located in first end 32 of receptacle 24, and a second electrode 42 is shown as being located in second end 34 of receptacle 24. First electrode 40 and second electrode 42 each comprise a metal strip disposed on floor 28 of receptacle 24.

A battery 44, or other power source is electrically coupled between first and second electrodes 40 and 42, such that first electrode 40 comprises a negative pole and second electrode 42 comprises a positive pole. The electric field generated between first and second electrodes 40 and 42, is non-alternating, but the use of an alternating power source in place of battery 44 would be acceptable.

When DNA is the microstructure being induced to migrate, the electric field intensity in receptacle 24 is in the range of from about 0.1 volt per centimeter to about 20 volts per centimeter.

In FIG. 3, the portion of FIG. 2 encircled by line 3—3 is illustrated in an enlarged manner. FIG. 3 illustrates one example of a means for use in a sorting apparatus of the present invention. As shown, array 38 comprises a plurality of obstacles 39 upstanding from floor 28 of receptacle 24. Although FIG. 3 illustrates obstacles 39 as being positioned within array 38 in an ordered and uniform pattern, staggered patterns, or any other predetermined and reproducible pattern, are employable.

FIG. 4 illustrates the various dimension of a typical obstacle 39. The height H of obstacle 39 is measured in a direction normal to floor 28 of receptacle 24. The length L of obstacle 39 is measured in a direction parallel to said migration direction M. The width W of obstacle 39 is measured in a direction normal to the migration direction M. Each of the obstacles 39 are separated from an adjacent obstacle 39 by a predetermined separation distance $S_d$. The space between adjacent of obstacles 39 is a cross section of array 38 taken normal to floor 28 of receptacle 24 defines a pore 54 of the lattice structure cumulatively produced by obstacles 39 of array 38. For convenience of reference in FIG. 4, such a typical pore 54 has been shaded.

FIG. 4A, a cross-section of two obstacles 39, illustrates in planar view a typical pore 54. Pore 54 compresses the area defined by two obstacles 39 through which a microstructure must pass. Pore 54 is defined by the height H and the separation distance $S_d$ between the obstacles. The desired size of pore 54 is determined by reference to the size of the microstructures to be sorted therethrough. Not only is the pore size of the arrays known, but it is also constant and reproducible.

These dimensions can be changed and designed to be as desired depending upon the type and size of microstructure to be sorted, the design of the array, and the type of obstacles in the array.

For example, the separation distance $S_d$ will vary depending upon whether the migration of microstructures through pores 54 are DNA molecules, viruses and bacterial cells, or mammalian cells. For migration of DNA molecules, the separation distance $S_d$ is within the range of about 0.01 microns to about 20.0 microns. For migration of viruses and bacterial cells, the separation distance $S_d$ is within the range of about 0.01 microns to about 1.0 micron. For migration of mammalian cells, the separation distance is within the range of from about 1.0 micron to about 50.0 microns. It is presently preferred that the separation distance $S_d$ be substantially equal to the radius of gyration of the molecule, the radius of gyration being the distance walking out from the center of the molecule.

Length L also varies depending upon the microstructure to be migrated through array 38 of obstacles 39. In a presently preferred embodiment, the length is generally equal to the separation distance. With regard to height H, the height of obstacles may generally be in the range of from 0.01 microns to about 20.0 microns. For smaller microstructures, the obstacles may have a height in a range from about 0.01 microns to about 0.50 microns. For larger microns, the height may be in the range from about 1.0 micron to about 5.0 microns.

In FIG. 5, another embodiment of an array of obstacles can be seen that is particularly suitable for sorting larger microstructures, such as free cells, viruses, or minute particles. There an array 60 of obstacles in the form of elongated rectangular bunkers 62 is positioned within receptacle 24. Bunkers 62 are comprised of a rectangular shape having opposing sidewalls 64 and a top 66. Bunkers 62 upstand from floor 28 of receptacle 24. bunkers 62 are positioned within columns and rows within receptacle 24. Cells, for example, migrate through the columns and between the rows of bunkers 62 in a migration direction indicated by arrow M. The longitudinal axis of bunkers 62 is disposed in alignment with migration direction M. Channels 68 are formed between rows of bunkers 62 of width W through which the cells migrate. A separation distance $S_d$, between adjacent rows of bunkers 62 indicates the size of channels 68.

The size and organization of bunkers 62 may vary. Thus, the separation distance $S_d$ may be sized to allow the cells to migrate through channels 68 in essentially a single layer in at least one single file.

The height H of each bunker 62 should also be such as to allow the cells to pass through the bunkers 62 in essentially a single layer. As with sorting apparatus 20, a coverslip 36 is fused to the tops 66 of bunkers 62 to prevent migration of cells between the coverslip and the tops 66 of bunkers 66. This ensures that the cells migrate through the array 60 of bunkers 62 in essentially a single layer.

Bunkers 62 are but examples of obstacles for forming channels 68. Different structures may also be used to simulate channels through which the cells can migrate and be observed.

One known method for making apparatus of the type discussed above involves forming receptacle 24 on one side of substrate 22. Receptacle 24 should be formed of a size such that microstructures migrate in the fluid through receptacle 24 in essentially a single layer. A further step comprises creating array 38 of obstacles 39 within receptacle 24. Each of obstacles 39 have a top 56, sides 57, and a bottom end 58. Obstacles 39 are upstanding from floor 28 of receptacle 24 in a predetermined and reproducible pattern. In one embodiment, the array of obstacles may comprise a plurality of posts.

The creation of obstacles, such as posts, or bunkers, within the receptacle is illustrated in FIGS. 5A–5F. As shown in FIG. 5A, the forming step comprises developing a photosensitive photoresist layer 70 over areas of substrate 22 that are intended to correspond to tops 56 of obstacles 39. This is accomplished by exposing substrate 22 to light through a mask having thereon a corresponding opaque pattern.

The portion of photoresist layer 70 which is exposed to light becomes soluble in a basic developing solution, while the unexposed portion remains on substrate 22 to protect substrate 22. Thus, after development in the developing solution, substrate 22 is left with a pattern of photoresist layer 70 that is identical to the opaque pattern of the mask.

FIG. 5B illustrates substrate 22 with photoresist layer 70 thereon after exposure to light and development in solution.

The next step comprises etching substrate 22 such that the areas of substrate 22 unshielded by photoresist layer 70 are exposed to the etching, thereby forming receptacle 24. The array 38 of obstacles 39 upstanding within the etched receptacle 24 is formed by the portions of substrate 22 shielded by photoresist layer 70. FIG. 5C illustrates formation of receptacle 24 and the obstacles 39.

As can be seen in FIG. 5C, as the substrate 22 is etched, the photoresist layer 70 is also etched, but at a slower rate. FIG. 5C illustrates the receptacle 24 half formed, and photoresist layer 70 partially etched away. If, for example, the photoresist layer is etched at a rate $\frac{1}{10}$ the rate that substrate 22 is etched, the resulting receptacle can at most have a depth ten times the thickness of the photoresist layer. The thickness of photoresist layer 70 must therefore be chosen accordingly.

The etching process can be terminated at any time when the desired depth of the receptacle is reached. As illustrated in FIG. 5D, there may be some photoresist layer 70 still present on substrate 22 when the etching is terminated. If so, the next step is then dissolving photoresist layer 70 from substrate 22. This step leaves a clean substrate 22 as shown in FIG. 5E.

Etching may be effected by many methods. In the preferred embodiment, ion milling is used such that an overhead ion beam is used to etch the substrate 22 and photoresist layer 70. Other methods of etching, such as chemical etching, are also within the scope of the present invention.

The important step of fusing coverslip 36 to substrate 22 is illustrated in FIG. 5F as comprises positioning coverslip 36 over array 38 of obstacles 39, such that coverslip 36 is in contact with each of obstacles 39, and then applying an electric field between coverslip 36 and each of obstacles 39. The coverslip 36 is held with a negative potential. The obstacles 39 are held at a positive potential. Ions are thereby induced to migrate there between to create a bond between coverslip 36 and each of obstacles 39 at all areas of contact. The process of this step is referred to as field assisted fusion.

The voltage used to fuse coverslip 36 to the substrate 22 is preferably about 1 kilovolt but can be within the range of from 200 volts to about 2000 volts. The time for fusion is about 30 minutes at a temperature of about 400° C. The temperature can also range from about 300° C. to about 600° C., with 400° C. being the preferred temperature. In one embodiment, the coverslip comprises a Pyrex material. For example, sapphire, and quartz are materials which may also be used for the coverslip. Any ceramic material or an opaque material may also serve.

In the context of using field assisted fusion to secure the coverslip and substrate, it is advisable that the material used for coverslip 36 have substantially the same coefficient of thermal expansion as substrate 22. Otherwise, at the high temperature of fusion, the coverslip 36 and the substrate 22 will expand at different rates and a seal between the two would be difficult or impossible to accomplish.

Successful fusion can be tested by injecting a fluorescent fluid into the apparatus. A completely fused coverslip will not allow passage of any fluorescent fluid between coverslip 36 and obstacles 39.

The method of making the apparatus disclosed above, by involving Pyrex-silicon based anodic bonding to enclose the microstructure, entails high temperatures and high voltage conditions, either of which can damage components. The binding of the cover of the apparatus to the array thereof renders the resulting apparatus usable only once.

As the sealing of the structure is irreversible, access is precluded to sorted microstructures inside the structure, unless the device is destructively disassembled.

BRIEF SUMMARY OF THE INVENTION

It is an object of the present invention to provide further methods and apparatus for fractionation of microstructures.

Another object of the present invention is to provide improved microstructure sorting devices and associated methods.

An additional object of the present invention to provide a method for accessing sorted microstructures or particles inside a microfabricated microstructure sorting device, thereby to permit further analysis of those sorted microstructures or particles.

An additional object of the present invention is to provide further methods for making microstructure sorting devices.

Additional objects and advantages of the invention are set forth hereinbelow in the detailed described or will be appreciated by the practice of the invention.

To achieve the foregoing objects, and in accordance with the invention as embodied and broadly described herein, the present invention is directed to a method for hermetically and reversibly sealing a microfabricated sorting array. The cover and the microfabricated sorting array are nondestructively separable, allowing access to any sorted microstructures or particles therein and allowing the reuse after cleaning of the sorting array.

The present invention utilizes a silicone elastomer in various combinations with rigid materials, such as silicon. A microfabricated sorting array may be constructed photolithographically from a material such as silicon, or may be formed from an elastomeric material as, for example, by casting from a correspondingly configured microfabricated mold of silicon or of elastomer. Reversible sealing allows for access to the fractionated microstructures within the array.

Thus provided is an apparatus for sorting microstructures in a fluid medium. The apparatus includes a substrate having a floor bound on opposite sides by first and second side walls. The floor and the first and second side walls define a receptacle. Means are positioned within the receptacle for showing the rate of migration of microstructures within the receptacle. A cover that seals said receptacle and contacts the ends of the means opposite from the floor of the receptacle, is selectively separable therefrom. One of the cover or the substrate is comprised of an elastomer. The other may be comprised of silicon, quartz, sapphire, or even an elastomer.

In alternative embodiments of the invention, an apparatus for sorting microstructures in a fluid medium includes a rigid support backing for either of the substrate or the cover that is comprised of an elastomer.

Also disclosed according to the teachings of the present invention is a method of manufacturing an apparatus for sorting microstructures in a fluid medium. The method includes a step of providing a substrate having a floor bounded by opposed first and second side walls. The floor in combination with the first and second side walls defines a receptacle. In the receptacle, means are provided for slowing the rate of migration of microstructures through the receptacle. The method further comprises the steps of forming a cover and removably engaging the cover with the receptacle and with the ends of the means opposite from the floor of the receptacle.

The present invention thus provides methods and apparatus that facilitate the fractionation and study of many types of microstructures. The present invention allows the successful fractionation of DNA molecules of chromosomal length in quantities so small as to isolate single of those molecules. The present invention also facilitates the fractionation of larger microstructures, such as red blood cells.

The fractionation of other macromolecules and microstructures, such as proteins, polymers, viruses, other cells, and minute particles, is also considered to be within the scope of the present invention, however.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 15 is a cross-sectional elevation view of a peripheral portion of the sorting apparatus of FIG. 14 taken along section line 15—15 shown therein;

FIG. 16 is a cross-sectional elevation view similar to that of FIG. 15 in which a portion of the elastomeric array of obstacles of the illustrated sorting apparatus has been nondestructively separated from the cover of that sorting apparatus;

FIGS. 17A–17F illustrate steps in a method for manufacturing a sorting apparatus, such as the sorting apparatus illustrated in FIGS. 14–16;

DETAILED DESCRIPTION OF THE PREFERRED EMBODIMENTS

For brevity and simplicity, methods and apparatus incorporating teachings of the present invention will be disclosed in relation to the use thereof in connection with white blood cell fractionation. It should be understood, however, that the use of the methods and apparatus of the present invention in that relation is provided merely by way of example of the multiple purposes toward which the methods and apparatus of the present invention advantageously finds utility.

Figure 1:
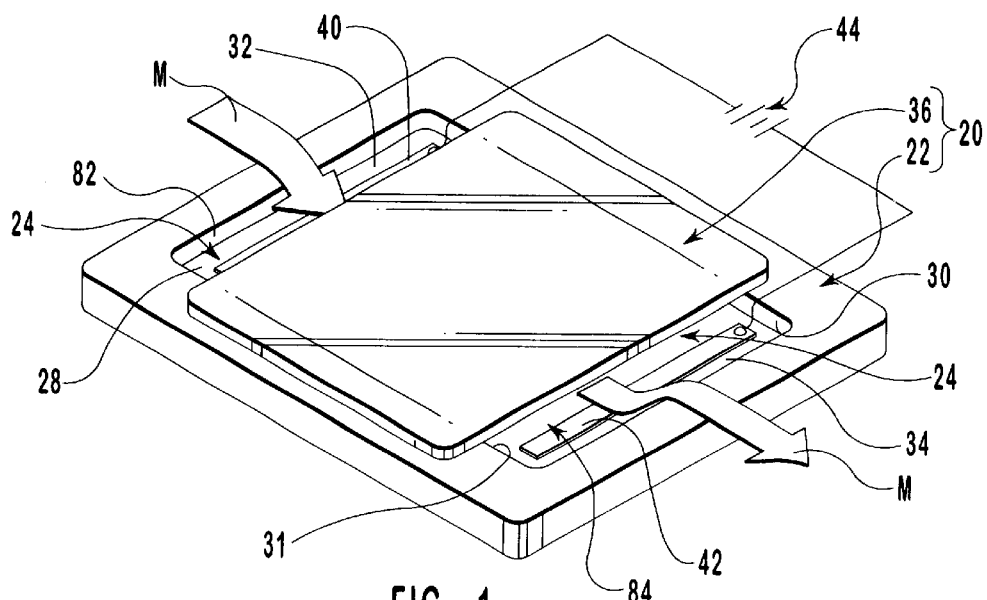
FIG. 1 is a perspective view of one embodiment of a known sorting apparatus.
Figure 2:
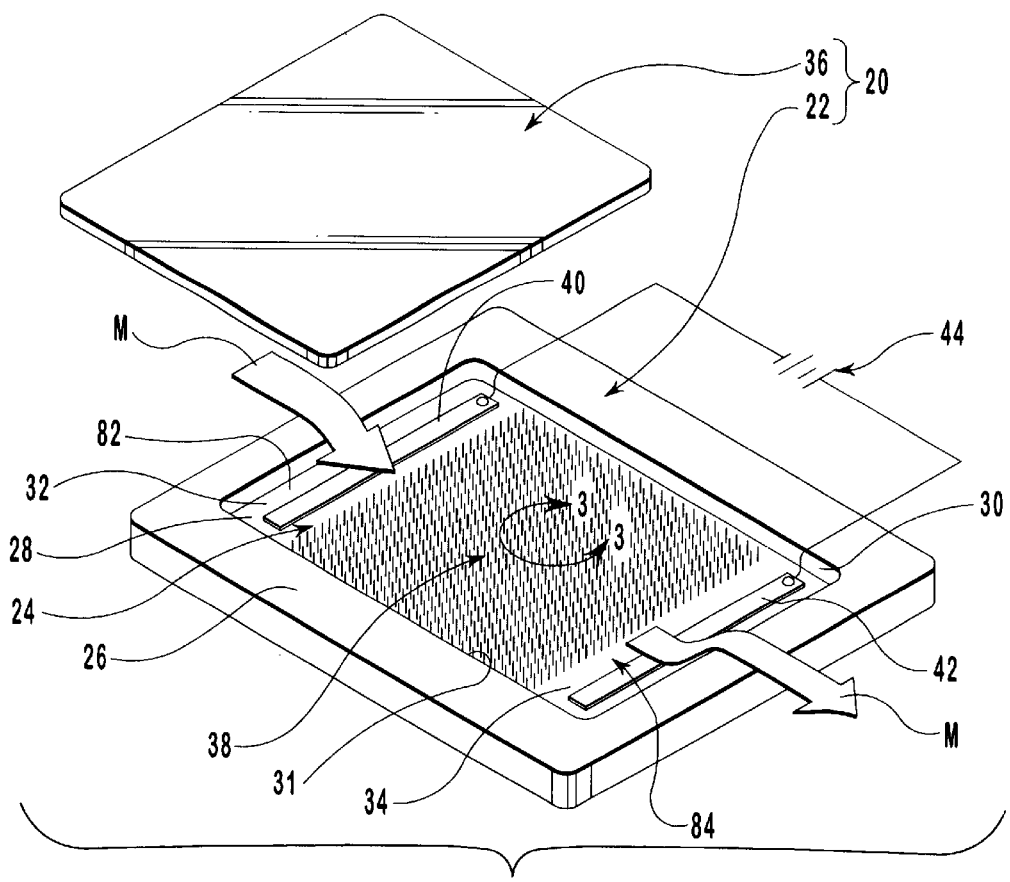
FIG. 2 is an exploded perspective view of the apparatus illustrated in FIG. 1 with the coverslip thereof shown separated from the substrate to more fully reveal an array of obstacles therebetween.
Figure 3:
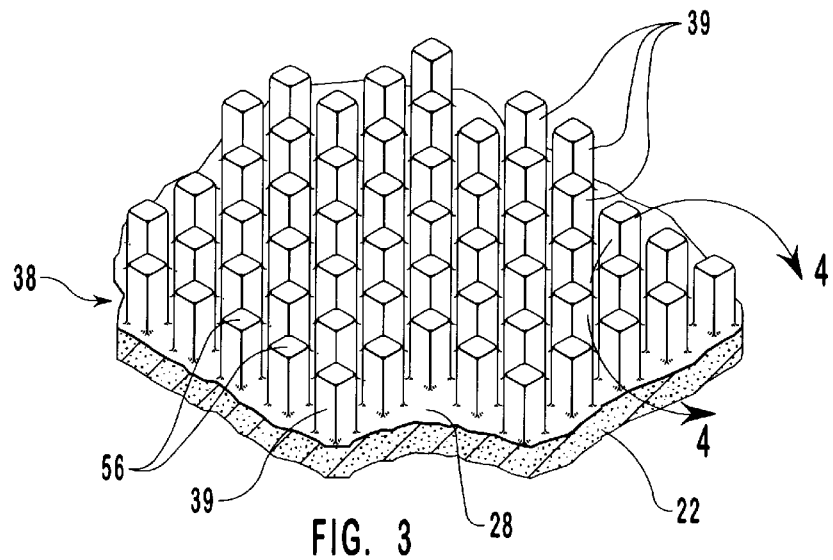
FIG. 3 is an enlarged perspective view of the obstacles within the area of the array of FIG. 2 encircled by line 3—3 therein.
Figure 4:
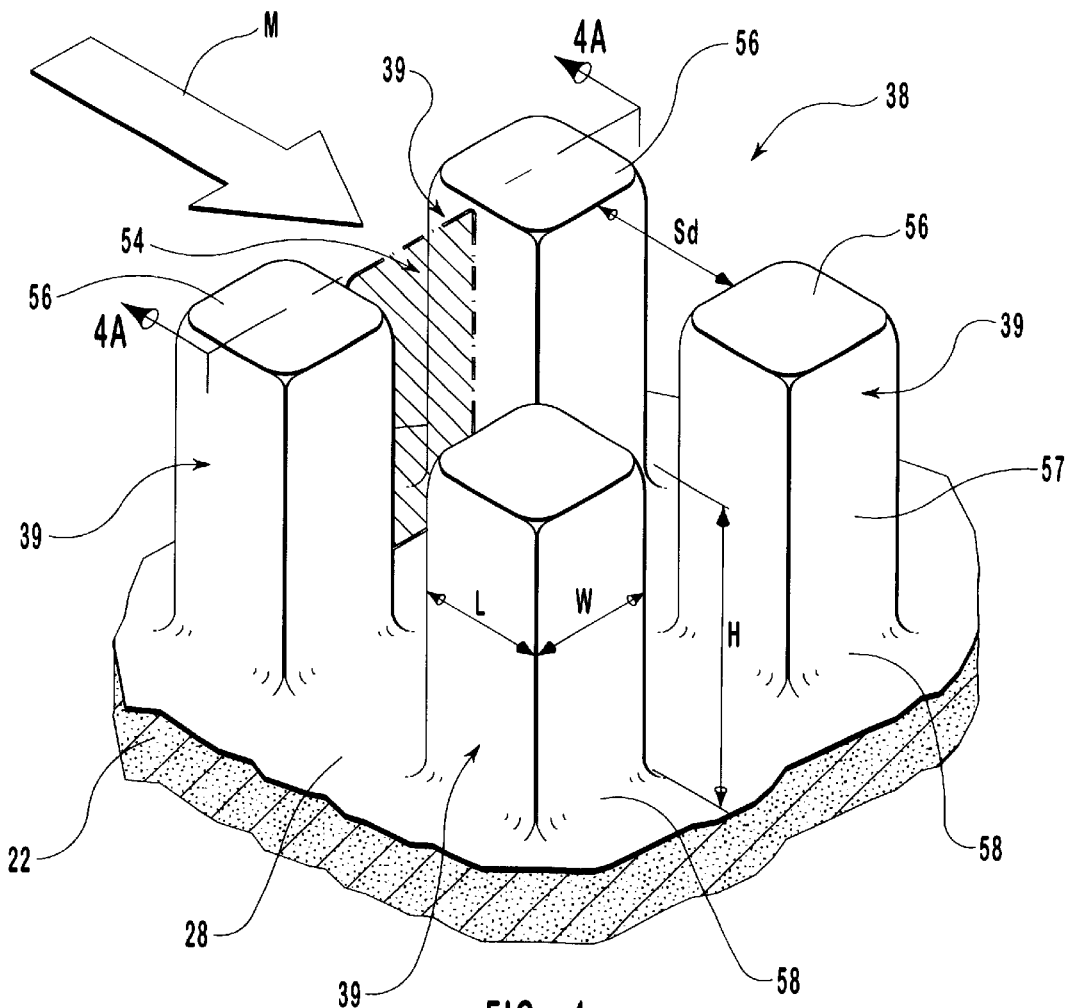
FIG. 4 is a further perspective enlarged view of the obstacles within the area of the array of FIG. 3 encircled by line 4—4 therein.
Figure 7:
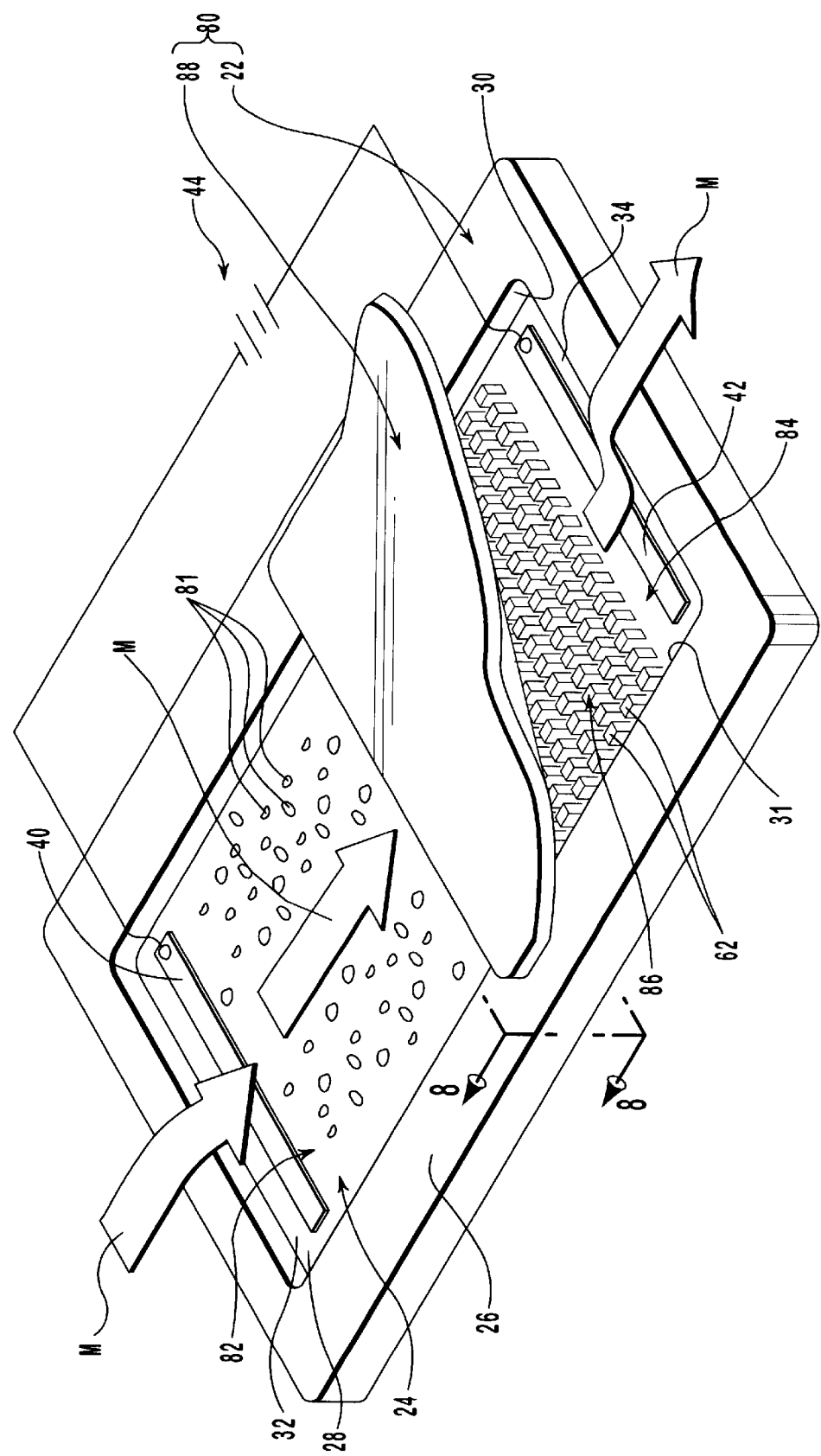
FIG. 7 is a perspective view of a first embodiment of a sorting apparatus incorporating teachings of the present invention.

FIG. 7 illustrates a first embodiment of a sorting apparatus 80 incorporating teachings of the present invention. Sorting apparatus 80 is similar in several respects to known sorting apparatus 20 illustrated in FIG. 1. Accordingly, structures in sorting apparatus 80 that are substantially identical to structures already identified in sorting apparatus 20 will be identified by the same terminology and reference characters as was utilized in relation to sorting apparatus 20.

Sorting apparatus 80 is comprised of an elongated substrate 82 having a correspondingly elongated receptacle 24 located on a side 26 thereof. A number of living cells 81 to be fractionated in sorting apparatus 80 are shown in a first loading area 82 moving in migration direction M toward a second loading area 84 at the opposite end of receptacle 24. The movement of cells 81 occurs in a fluid medium, which for simplicity is not shown.

It should be noted in addition that, while first electrode 40, second electrode 42, and battery 44 are illustrated as a set of structures that provide an electrophoretic-type of mobility to cells 81, this set of structures is presented by way of example as being but one of many sets of structures by which microstructures could be induced to move in migration direction M. Additional approaches to inducing the migration of microstructures can include induced forced fluid flow, gravity, and other techniques. Induced fluid flow is used extensively with large microstructures, such as cells 81, while electrophoretic-types of mobility are common in the sorting of smaller microstructures, such as DNA molecules.

Figure 5:
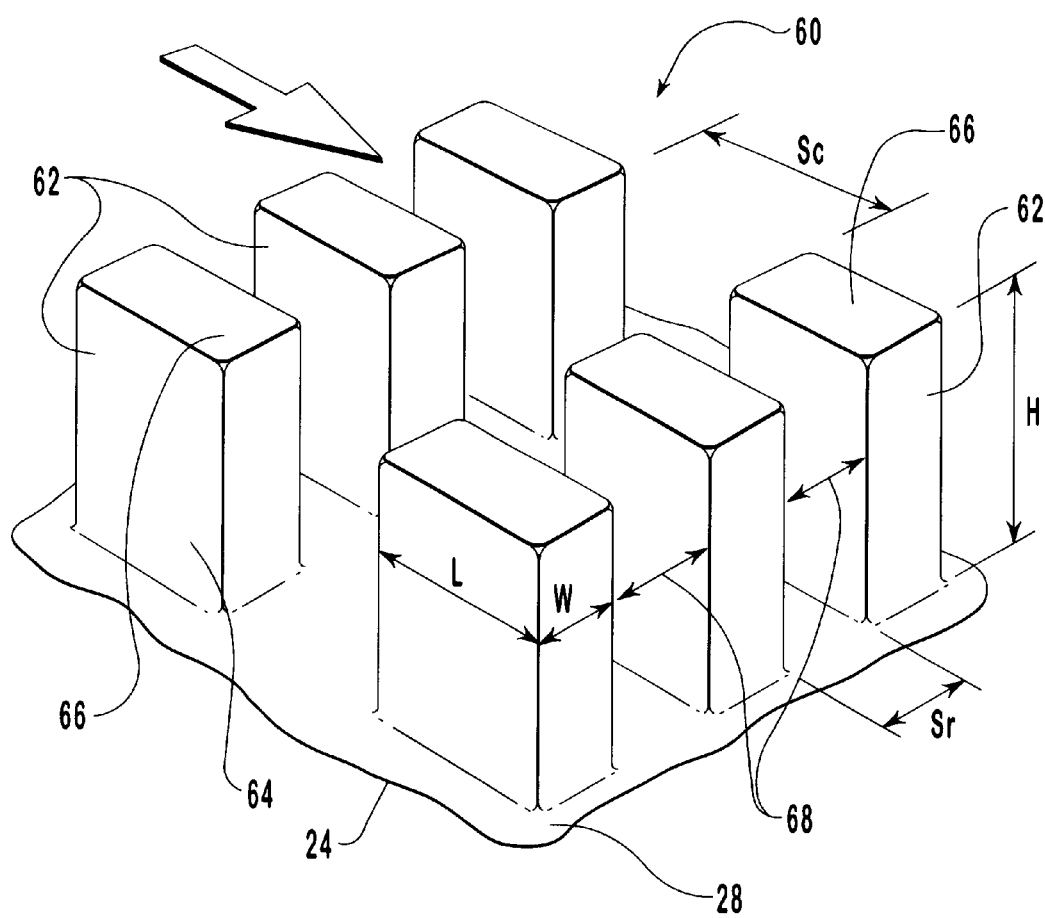
FIG. 5 is a perspective enlarged view of an alternate embodiment of obstacles for an array in a sorting apparatus that may be used to simulate the behavior of cells traveling through narrow passageways in the human body.
Figure 6A:
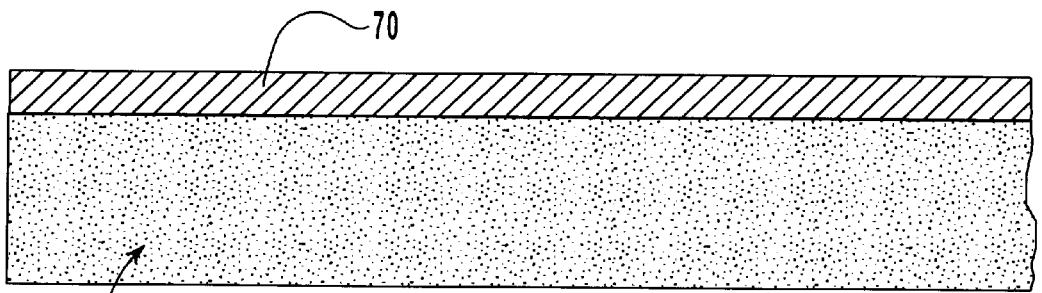
FIGS. 6A–6F illustrate steps in a method for manufacturing known sorting apparatus, such as known sorting apparatus of FIGS. 1–5.
Figure 6B:
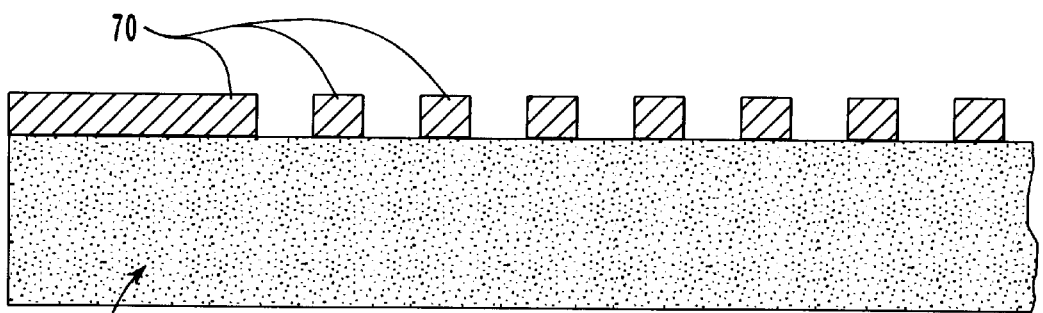
Figure 6C:
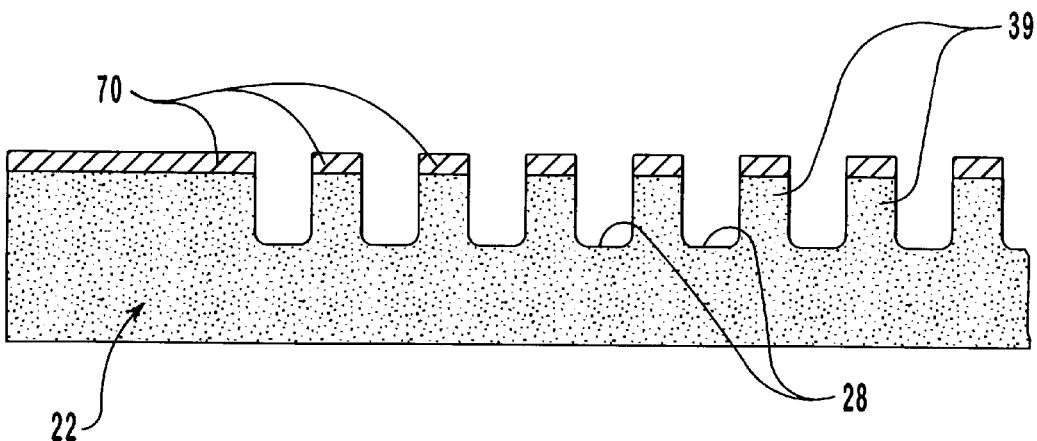
Figure 6D:
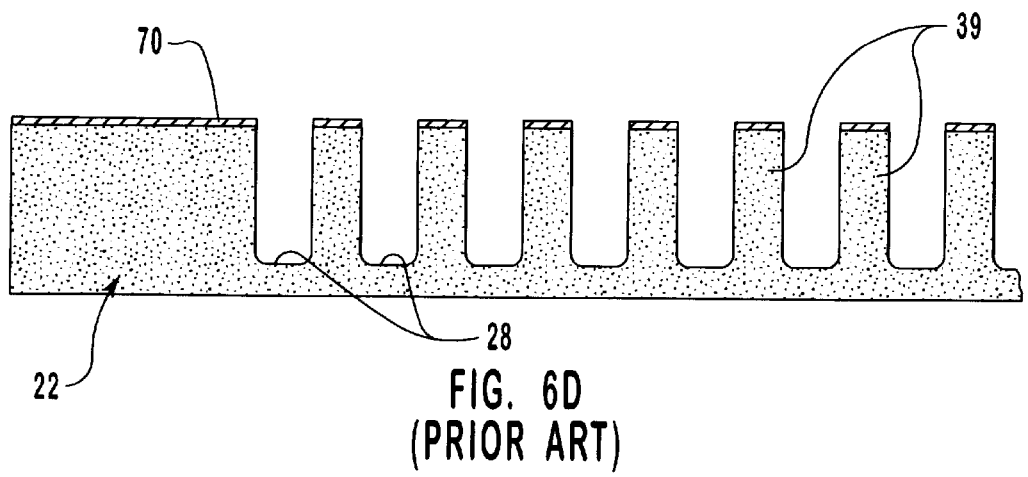
Figure 6E:
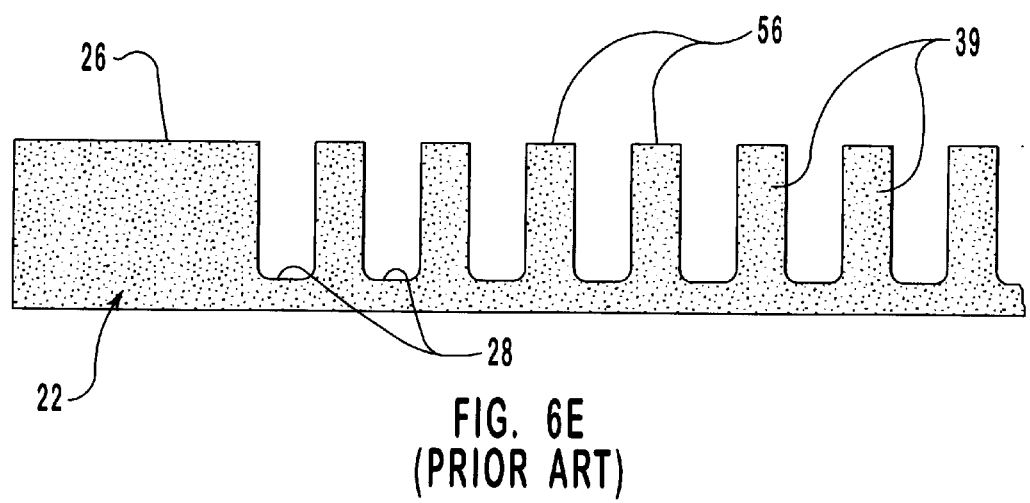
Figure 6F:
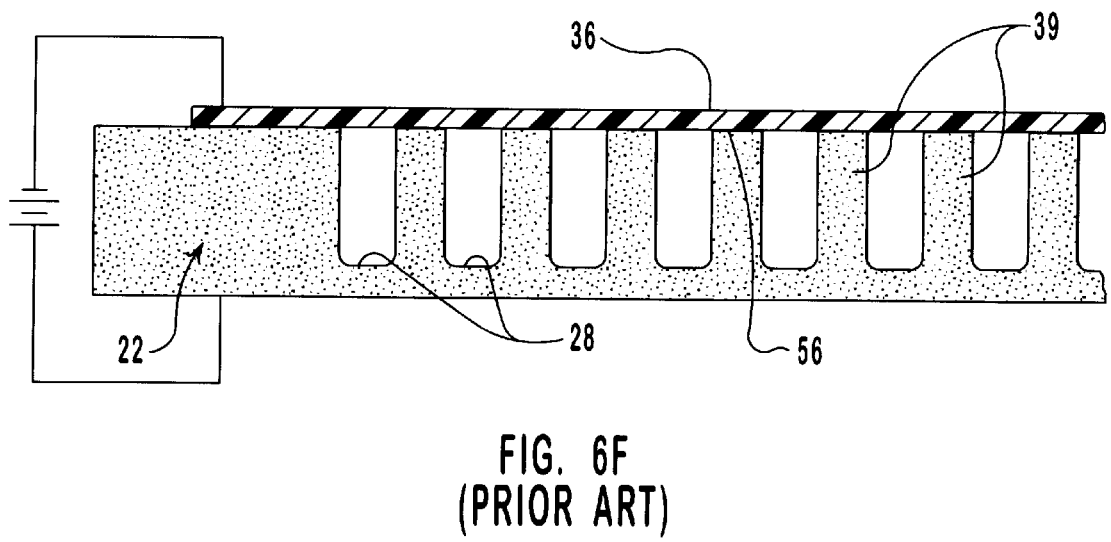

To migrate from first loading area 81 to second loading area 84, however, cells 81 pass through and interact with an array 86 of obstacles taking the form of bunkers 62 of the type illustrated in FIG. 5. Sorting apparatus 80 is provided with an elastomeric cover 88 that engages tops 66 of each bunker 62 in array 86. In contrast to rigid coverslip 36 illustrated in FIG. 1, elastomeric cover 88 is both flexible and nondestructively removable from the position thereof shown in FIG. 7. Typically, elastomeric cover 88 is formed from an appropriate elastomer in a manner to be disclosed subsequently. Elastomeric cover 88 may, if desired, be rendered transparent to permit viewing of the migration of cells 81 through array 86. Nonetheless, elastomeric cover 88 can be selectively lifted away from substrate 22 in the manner also illustrated in FIG. 7, thereby affording physical access to any specific fractionated portion of the collection of cells 81 migrating through array 86.

Figure 8:
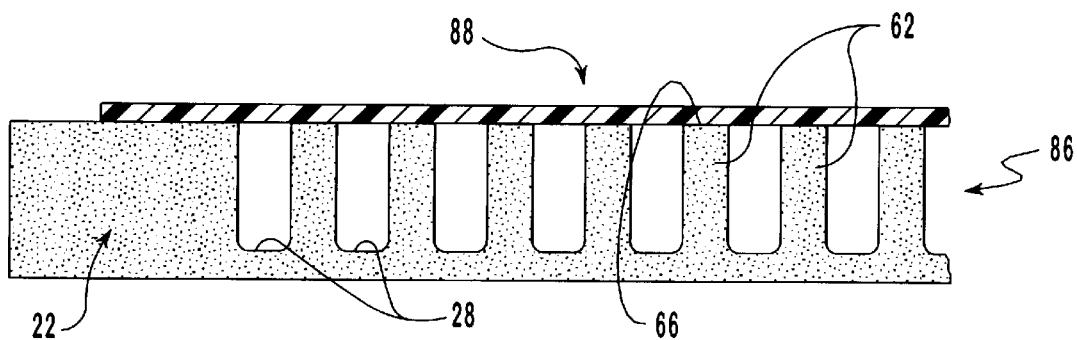
FIG. 8 is a cross-sectional elevation view of a peripheral portion of the sorting apparatus of FIG. 7 taken along section line 8—8 shown therein.
Figure 9:
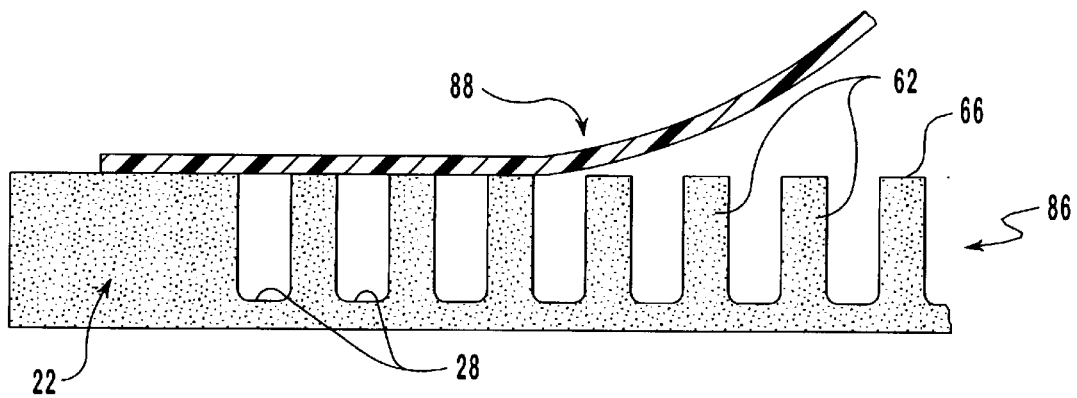
FIG. 9 is a cross-sectional elevation view similar to that of FIG. 8 in which the cover of the illustrated sorting apparatus has been nondestructively separated from a portion of the array of obstacles of that sorting apparatus.

These elements of sorting apparatus 80 are shown in the elevation cross section views of FIGS. 8 and 9 for enhanced clarity. In FIG. 8, elastomeric cover 88 is shown extending across and making contact with top 66 of each bunker 62 in array 86. In FIG. 9, a portion of elastomeric cover 88 is shown uplifted from top 66 of some of bunkers 62 to afford access to the interior of array 86.

Figure 10A:
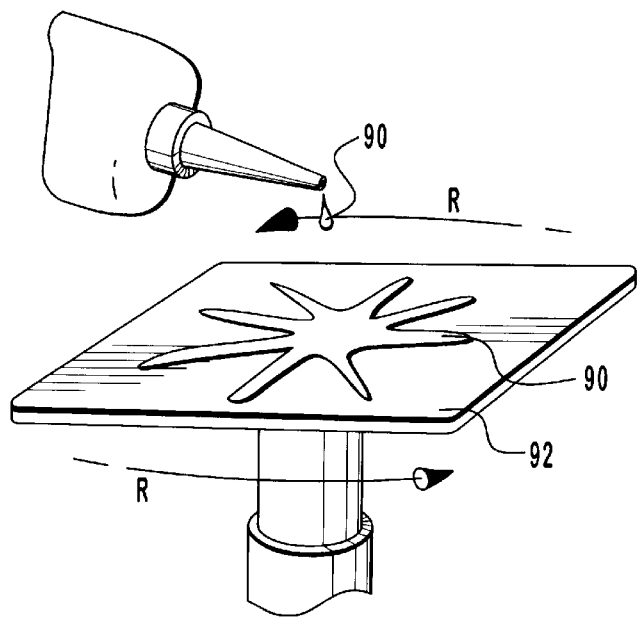
FIGS. 10–10D illustrate the steps in a method for manufacturing a sorting apparatus, such as the sorting apparatus illustrated in FIGS. 7–9.
Figure 10B:
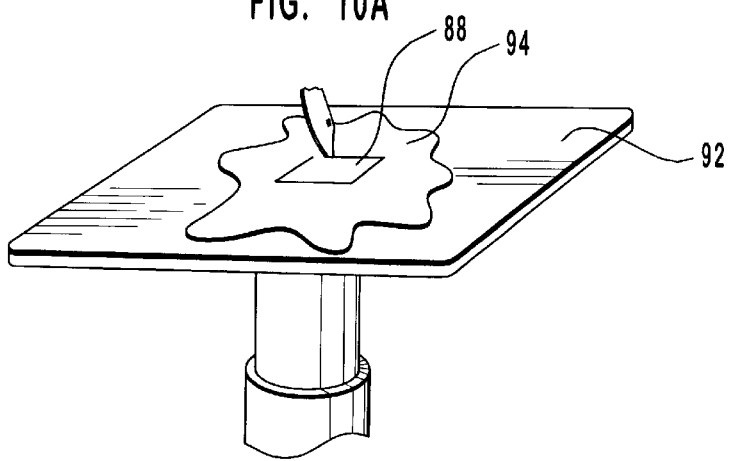
Figure 10C:
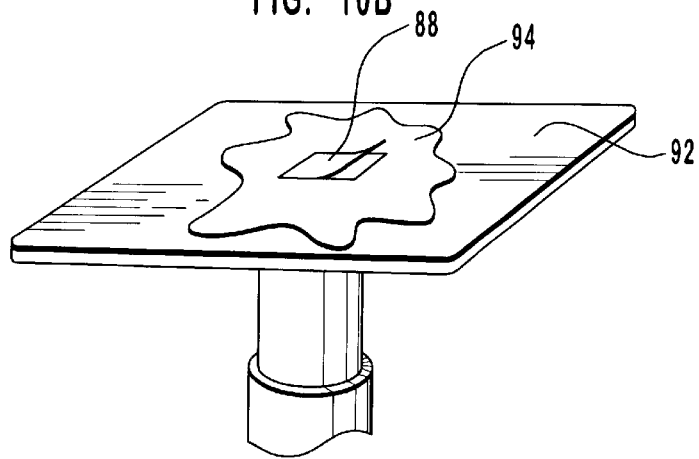

FIGS. 10A–10C illustrate steps in a method of manufacturing a selectively removable cover, such as elastomeric cover 88 of sorting apparatus 80. As shown in FIG. 10A, a liquid elastomer 90 is deposited on a flat surface 92, which is rotated in the plane thereof as indicated by the arrows R. As a result, liquid elastomer 90 is spread on surface 92 in a sheet of uniform thickness, which is then cured to produce a sheet of cured elastomer 94 shown in FIG. 10B.

As is also shown in FIG. 10B, the sheet of cured elastomer 94 is cut into a size and shape corresponding to elastomeric cover 88. Finally, elastomeric cover 88 is peeled out of the sheet of cured elastomer 94 and off of surface 92 and disposed across and in contact with the ends of array 86 of bunkers 62 opposite from floor 28 in the manner shown in FIGS. 7 and 8.

Figure 11:
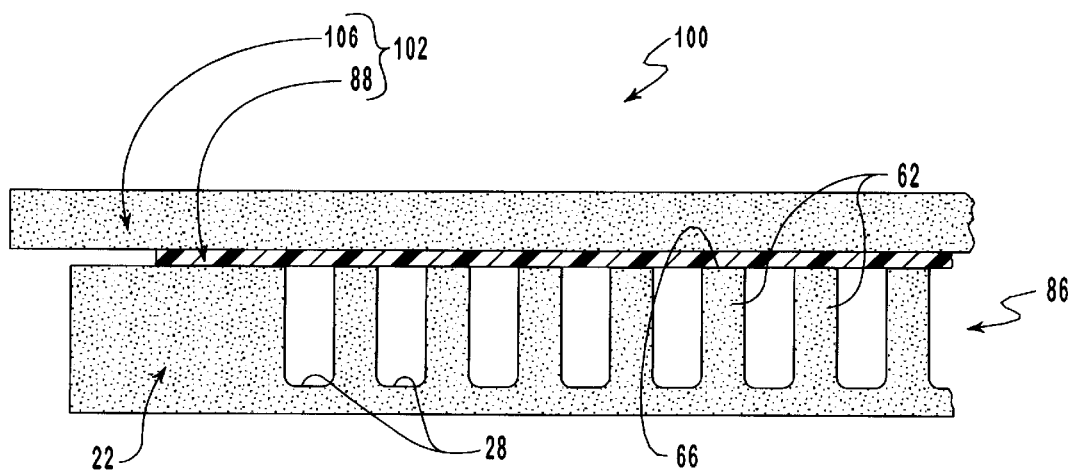
FIG. 11 is a cross-sectional elevation view of a peripheral portion of a second embodiment of a sorting apparatus incorporating teachings of the present invention.
Figure 12:
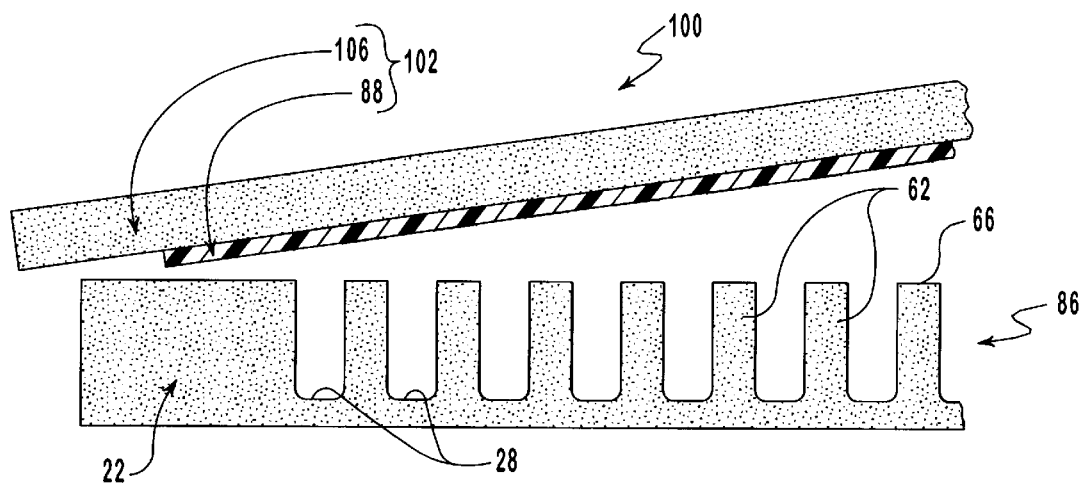
FIG. 12 is a cross-sectional elevation view similar to that of FIG. 11 in which the compound cover of the illustrated sorting apparatus has been separated from the array of obstacles of that sorting apparatus.

A second embodiment of a sorting apparatus 100 incorporating teachings of the present invention is illustrated in the elevation cross section views of FIGS. 11 and 12. In FIG. 11, sorting apparatus 100 is seen to include a compound cover 102 comprised of an elastomeric cover 88 carried on a flat surface 104 of a rigid cover support 106. Elastomeric cover 88 is of the type manufactured, for example, by the method illustrated in FIGS. 10A–10C. Cover support 106 like elastomeric cover 88 can be transparent. In contrast to elastomeric cover 88, however, cover support 106 is rigid, advantageously lending structural integrity to delicate elastomeric cover 88 during the placement of elastomeric cover 88 against tops 66 of bunkers 62 in the manner illustrated in FIG. 11.

A compound cover, such as compound cover 102 illustrated in FIG. 11, can be fabricated by adhering an elastomeric layer, such as elastomeric cover 88, to any suitable cover support after the elastomeric cover has been removed from a larger layer of cured elastomer, such as cured elastomer 94 illustrated in FIG. 10C. Alternatively, elastomer cover 88 need not be cut or removed from cured elastomer 94, if the structure carrying surface 92 illustrated in FIG. 10C is thereafter suitable for performing the function of cover support 106.

In FIG. 12, compound cover 102 is shown pivoted upwardly on the right of the figure, lifting elastomeric cover 88 from engagement with tops 66 of some of bunkers 62 to afford access to the interior of array 86. Once access to the interior of array 86 is no longer required, compound cover 102 can be lowered into the position thereof shown in FIG. 11, and the full, uninhibited use of sorting apparatus 100 may be resumed.

An alternative approach to the manufacture of a compound cover, such as compound cover 102, is illustrated in the sequence of elevation views shown in FIGS. 13A–13D.

Figure 13A:
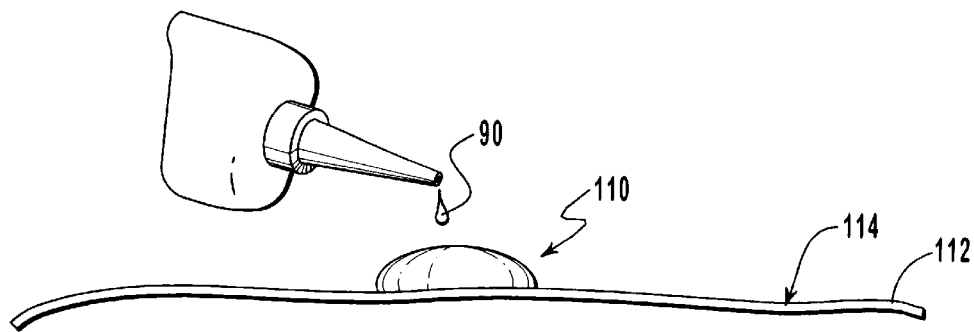
FIGS. 13A–13D illustrate steps in a method for manufacturing a sorting apparatus, such as the sorting apparatus illustrated in FIGS. 11–12.
Figure 13B:
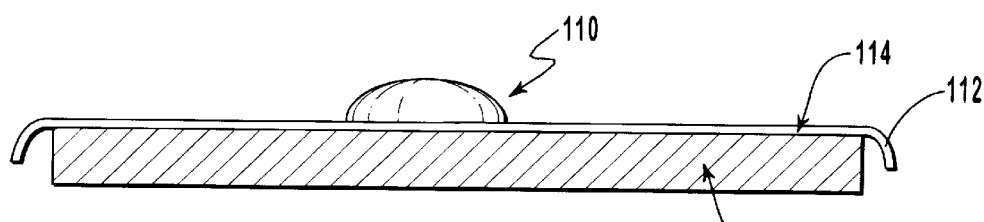
Figure 13C:
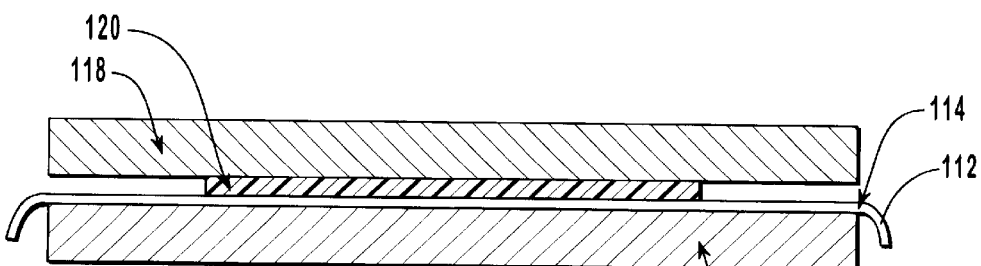
Figure 13D:
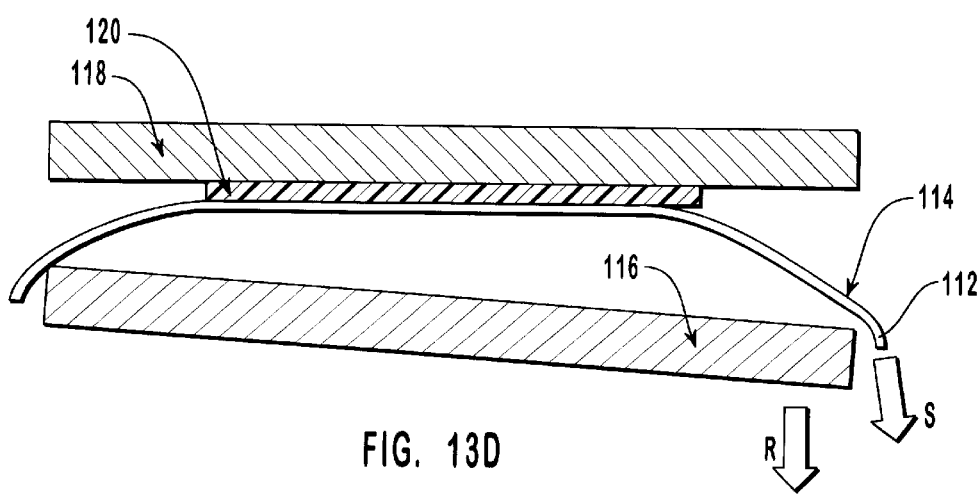

As shown in FIG. 13A, a liquid elastomer 90 is deposited as a bolus 110 on a surface 112 of a thin flexible sheet 114 of a material, such as cured plastic. Flexible sheet 112 is then rested on a rigid plate 116 in the manner illustrated in FIG. 13B. A second rigid plate taking the form of a cover support 118 is positioned on the opposite side of the assembly from rigid plate 116 and urged theretoward. This action compresses bolus 110 of liquid elastomer 90 into a thin sheet of uniform thickness, which is then cured forming an elastomeric cover 120. Finally, as suggested by arrow R in FIG. 13D, rigid plate 116 is removed from the assembly of FIG. 13C. Thereafter flexible sheet 14 can be peeled form elastomeric cover 120 as suggested by arrow S. The result is a second embodiment of a cover support 122 that is similar in many respects to cover support 106 shown in FIGS. 11 and 12.

Figure 14:
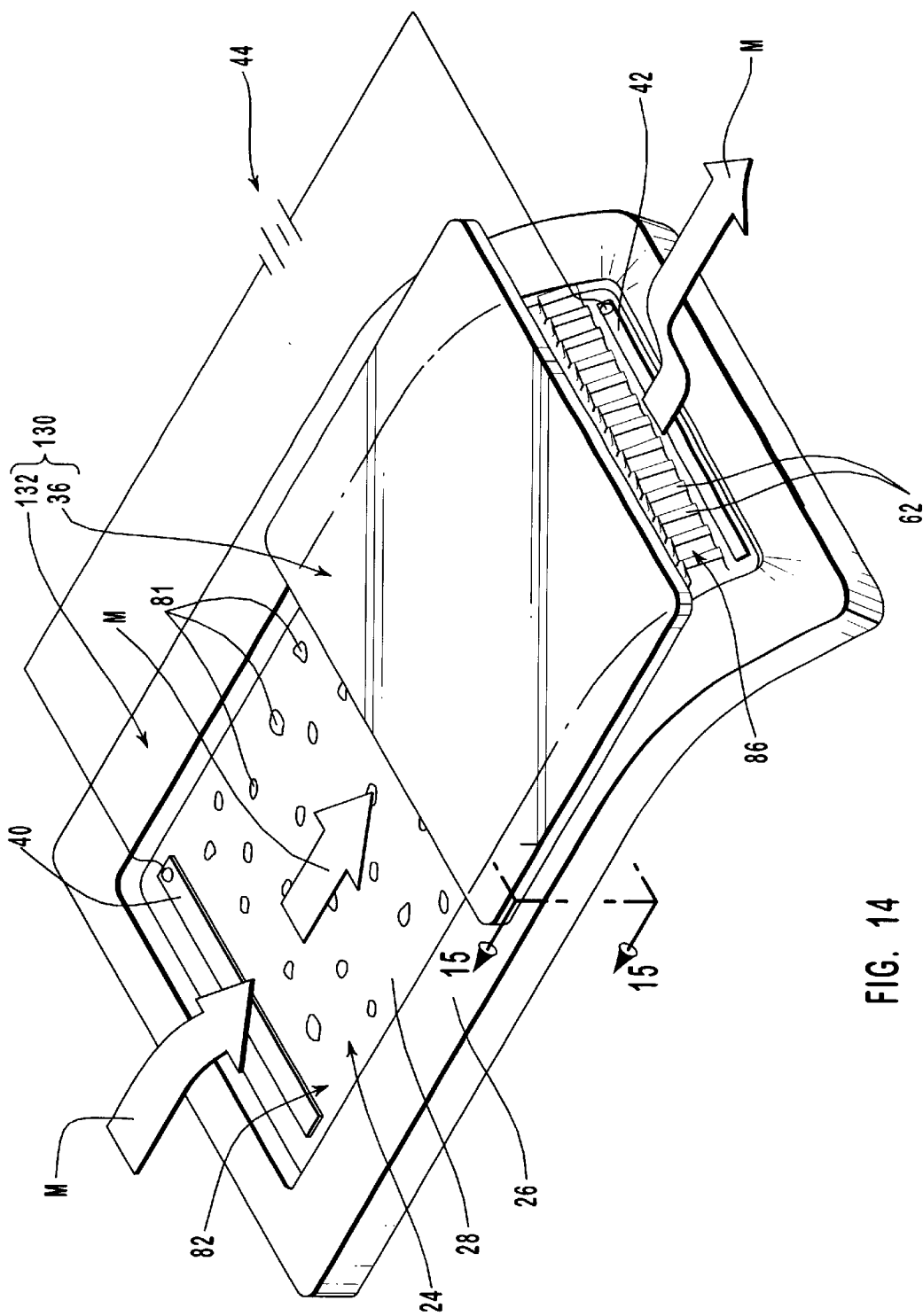
FIG. 14 is a perspective view of a third embodiment of a sorting apparatus incorporating teachings of the present invention.
Figure 17A:
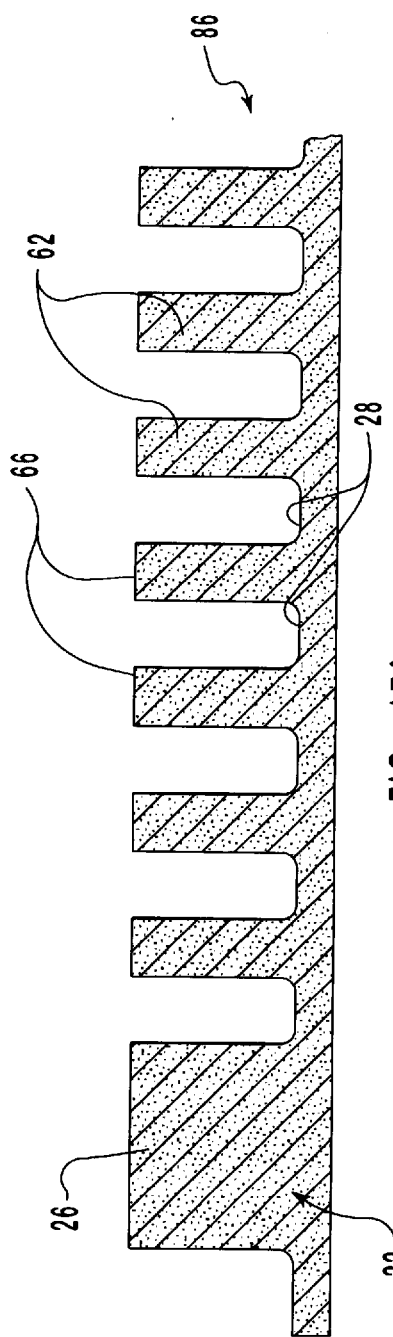
Figure 17B:
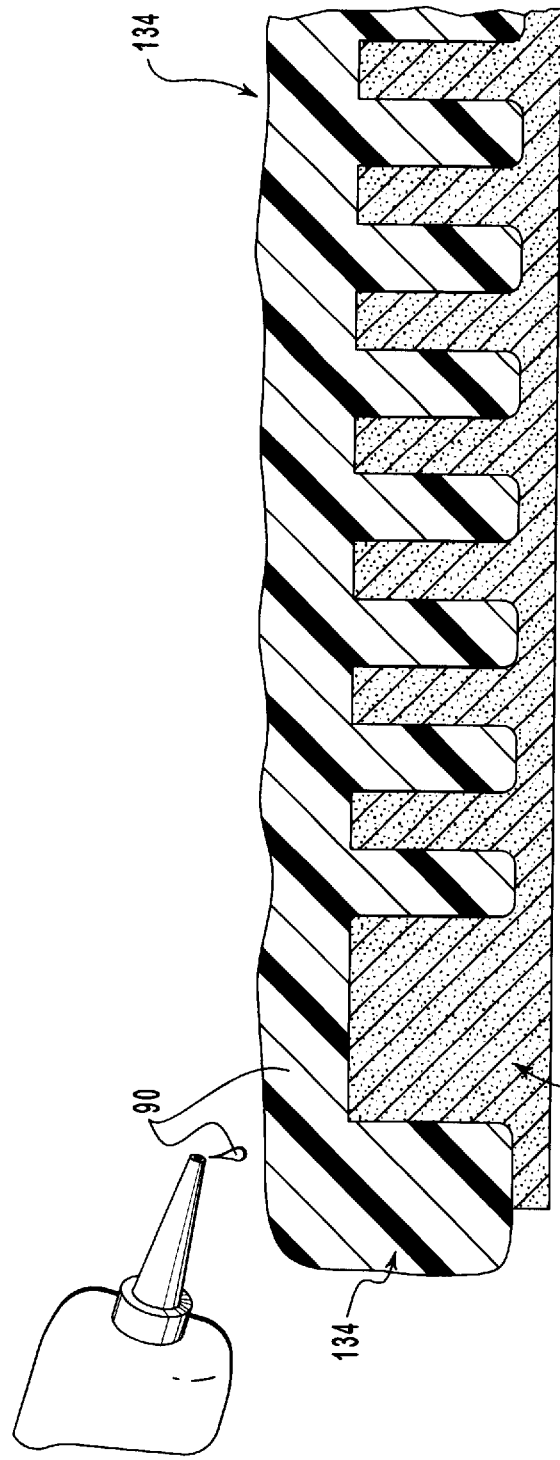

Yet another embodiment of a sorting apparatus 130, incorporating teachings of the present invention is illustrated in FIG. 14. Sorting apparatus 130 comprises a rigid coverslip 36 of the type illustrated in FIGS. 1–5 in combination with a flexible substrate 132 that is selectively detachable from coverslip 36 for the purpose of affording access to array 86 of bunkers 62 disposed below coverslip 36. Typically, substrate 132 and array 86 of bunkers 62 are formed of an elastomer of the type disclosed above as being useful in forming elastomeric covers 88 and 120.

FIGS. 15 and 16 illustrate selected of these relationships in sorting apparatus 130. In FIG. 15, rigid coverslip 36 can be seen disposed across and in contact with tops 66 of bunkers 62 in array 86. In FIG. 16, a portion of flexible substrate 132 has been moved downwardly, separating tops 66 of some bunkers 62 from coverslip 36.

A method of manufacturing a flexible substrate, such as flexible substrate 132, is illustrated in FIGS. 17A–17F.

In FIG. 14A, a rigid substrate, such as substrate 22, shown in FIG. 5F, is manufactured according to the microlityhographic techniques described in relation to FIGS. 5A–5F. Substrate 26 is not, however, utilized directly to provide an array of obstacles for use in sorting apparatus 130. Instead, substrate 22 is utilized as a mold in the manner shown in FIG. 17B upon which to cast a first quantity 134 of liquid elastomer 90, which is then cured. As illustrated in FIG. 17C, cured first quantity 134 of elastomer 90 is then removed from substrate 22 as shown by arrow A and upended into the position shown in FIG. 17D to be used as a negative mold 136 for producing a replica of rigid substrate 22.

Where the elastomer being utilized to form negative mold 136 is a silicone elastomer, it should be noted that the surface characteristics of negative mold 136 will be unacceptably hydrophobic. Procedures must be undertaken to convert the surface of a negative mold, such as negative mold 136, comprised of a silicone elastomer into a surface that is hydrophylic, and that is therefore markedly increased in a capacity to interact as required with other materials in the process illustrated in FIGS. 17A–17F. In one such procedure, negative mold 136 is placed in an oxygen plasma generator. There the ion bombardment of the surface of negative mold 136 by oxygen ions produces there minute deposits of $SiO_2$ that alter the ionic nature of the surface of negative mold 136 into a surface that is hydrophylic. Alternative methods for converting the surface of silicone structures into hydrophylic surfaces will be mentioned subsequently.

Where negative mold 136 is comprised of a silicone elastomer, it is also necessary before casting a silicone elastomer article therein to insure that the material of negative mold 136 does not attach to and heal with the material of the silicone elastomer article to be cast therefrom. Therefore, after the surface of negative mold 136 has been rendered hydrophylic, negative mold 136 is dipped in a detergent. This results in the surface of negative mold 136 becoming coated with a grease layer that prevents the adherence to negative mold 136 of any silicone elastomer cast thereupon.

Only then is it possible upon negative mold 136 to cast a desired second quantity 138 of elastomer 90, which is also then cured. As illustrated in FIG. 17E, cured second quantity 138 of elastomer 90 is removed from negative mold 136 as shown by arrow B and upended into the position shown in FIG. 17F. This results in the formation of an elastomeric substrate, such as flexible substrate 132, that supports an array 86 of upstanding bunkers 62 and that is an exact replica of array 86 on rigid substrate 22. Before use of array 86, however, the surface of substrate 132 must be treated as described above to render the surface of flexible substrate 132 hydrophylic. Then, rigid coverslip 36 may be removably disposed in contact with the tops of the elements of array 86 as suggested by arrows C.

Figure 18:
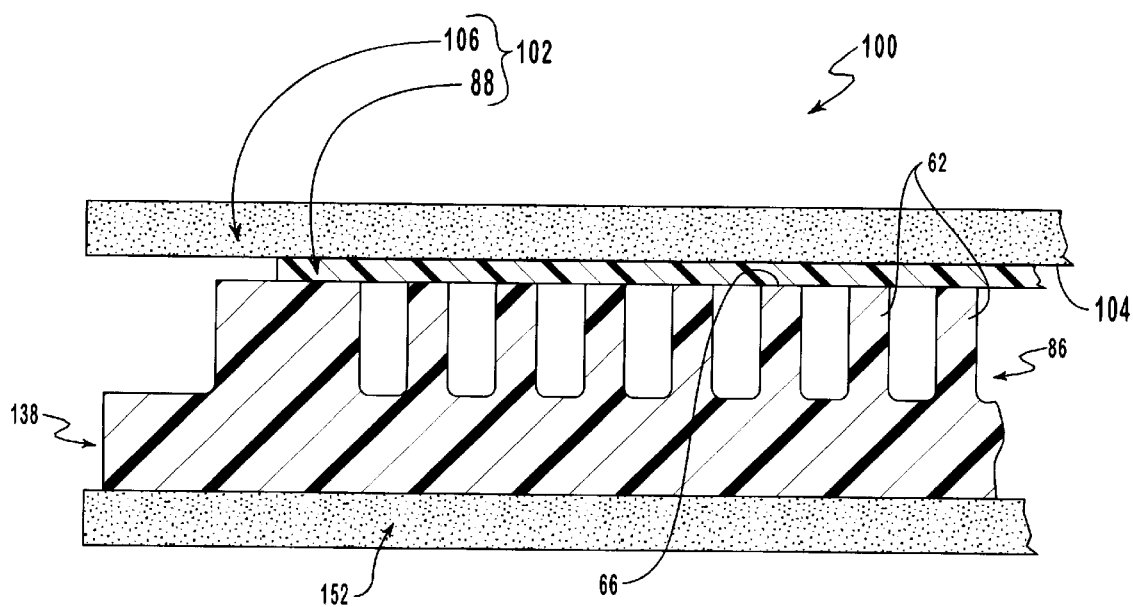
FIG. 18 is a cross-sectional elevation view of a fourth embodiment of a sorting apparatus incorporating teachings of the present invention.

Yet another embodiment of a sorting apparatus 150 incorporating teachings of the present invention is illustrated in FIG. 18. Sorting apparatus 150 comprises a flexible substrate 132 in combination with a compound cover 102 that includes elastomeric cover 88 supported on a planar surface 104 of a cover support 106. Compound cover 102 is thus selectively detachable from flexible substrate 132 for the purpose of affording access to array 86 of bunker 62 disposed below compound cover 102. Optionally, flexible substrate 132 can be structurally enhanced by the disposition of flexible substrate 132 on a substrate support 152 as also shown in FIG. 18. Access in sorting apparatus 150 to array 86 of bunker 62 is effected by pivoting compound cover 102 away from flexible substrate 132 much in the manner illustrated relative to compound cover 102 in FIG. 12.

The microlithographic methods discussed above were used to construct arrays of obstacles of silicon. The silicon arrays were cleaned in a 1/1/1 by volume mixture of boiling distilled water, hydrogen peroxide and ammonium hydroxide for 20 minutes. Five grams of General Electric silicone type RTV615 was mixed with catalyst and degassed in a vacuum oven, poured over a clean silicon wafer, degassed and cured at 80° C. for one hour. The cured elastomer was placed over the array, and spontaneous sealing occurred.

A diluted solution of hydrophilic polyurethane from Tyndale Plains Hunter Inc. was allowed to wet the sealed array at the open end and dried. In this manner, the surface of the cured elastomer facing the array and closing the top of fluid passageways therethrough was rendered sufficiently hydrophylic to admit fluid containing microstructures into the sorting array. Other polymers including hydrophilic polyether polyurethane, vinylpyrrolidone or polymers comprising acrylamide, acrylic acid, and/or hydroxyethylmethacrylate may also be used for this purpose. Saline buffer was then used to wet the sealed, coated array.

The self-sealing silicone elastomer successfully reversibly sealed the tops of photolithographically constructed arrays of synthetic microfabricated channels. Use of reversible sealing covers constructed of silicone elastomers allowed access to the fractionated cells within the array and the reuse of the array with or without cleaning thereof as appropriate to the intended use thereof.

Cells in the array did not stick to the elastomer lid which sealed the top of the array. This fact was observed by lifting the elastomer lid off the array and re-imaging the exposed cell using fluorescent. The cell density and pattern before and after removing the elastomer lid was not changed. Examination of the elastomer lid using epi-fluorescence after removal showed that no cells had adhered to the removed elastomer, confirming that the cells had specifically bonded to the polymer treated silicon structures. While adhesion of the cells to the coated silicon substrate may be due to either electrostatic interactions with the underlying silicon or cell protein/ligand binding to the polyurethane coating, the non-adhesion of the cells to the elastomer lid opens the exciting possibility that the fractionated cells can be individually removed from the array for further analysis, a crucial aspect of the removable lid technology developed herein. Exploitation of the potential of these devices for cell biology will require advances in both cell biology and understanding the physics of the deformation and adhesion of soft surfaces.

Figure 19:
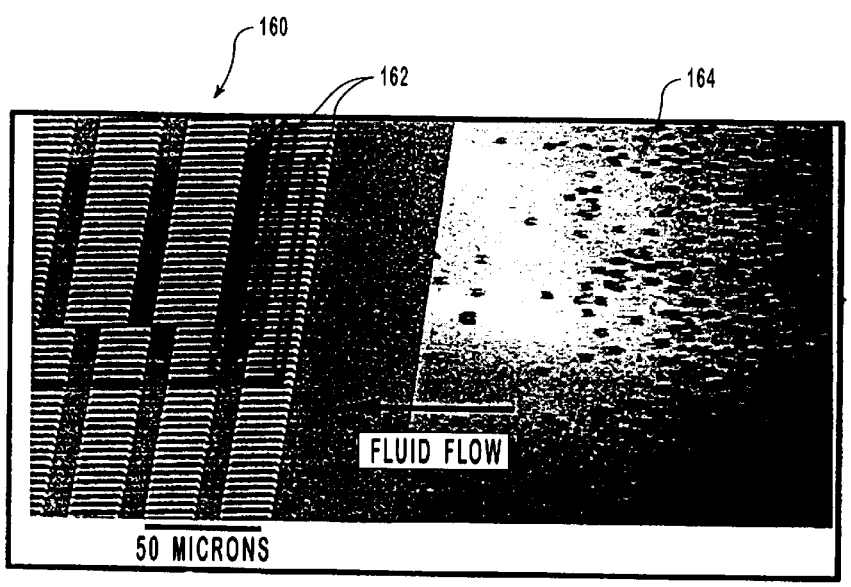
FIG. 19 is a scanning electron micrograph perspective view of a sorting device of the type illustrated in FIGS. 7–9 with a reversibly sealed elastomer cover schematically shown thereon.

FIG. 19 is a composite diagram of the appearance of such an array 160. Array 160 has channels with lengths varying from 20 μm to 200 μm in a stepwise fashion, with etched depth and width of 5×5 μm. The arrays were sealed hermetically on their top by placing a flat rectangle cover 162 of approximately 1 mm thick of silicon elastomer polydimethylsiloxane (PDMS) (Type RTV416, GE Polymers) over a clean, dry array. The reversibly sealed elastomer cover 162 is shown schematically in this figure overlying array 160 in both a flat and a partially raised position. Visualization of blood cells in the array was done using three techniques: (1) reflected epi-illumination, (2) epi-fluorescent imaging of cell nuclei using a DNA binding dye, benzimidazole (Hoechse dye 33342, or H22232) a vital nuclear stain, and (3) epi-fluorescent imaging of the external cell walls using fluorescent-labeling antibodies which are specific to selected type of leukocytes.

Array 160 of FIG. 19 was fabricated on a silicon wafer using a combination of $CHF_3$ etching with photoresist masks and CI etching using a $SiO_2$ mask. The etch depth was 5 microns. Superimposed on this micrograph is a representation of the polydimethylsiloxane (PDMS) elastomer cover 162 which seals the array, but which can be reversibly lifted from the surface of array 160 as shown. The PDMS was General Electric silicone type RTV615, cast on a silicon wafer surface followed by cutting and removal from the surface.

On the right hand side of FIG. 19 is an image taken epi-illumination of a leading front of red blood cells 164 approaching array 160. Hydrodynamic pressure gradients on the order of 5 $lb/in^2/in$ (or $3\times10^3$ Pa/cm) move erythrocytes easily through such a sealed array at a speed of about 1 mm/s, if the surfaces of array 160 have been properly chemically cleaned and conditioned.

Figure 20:
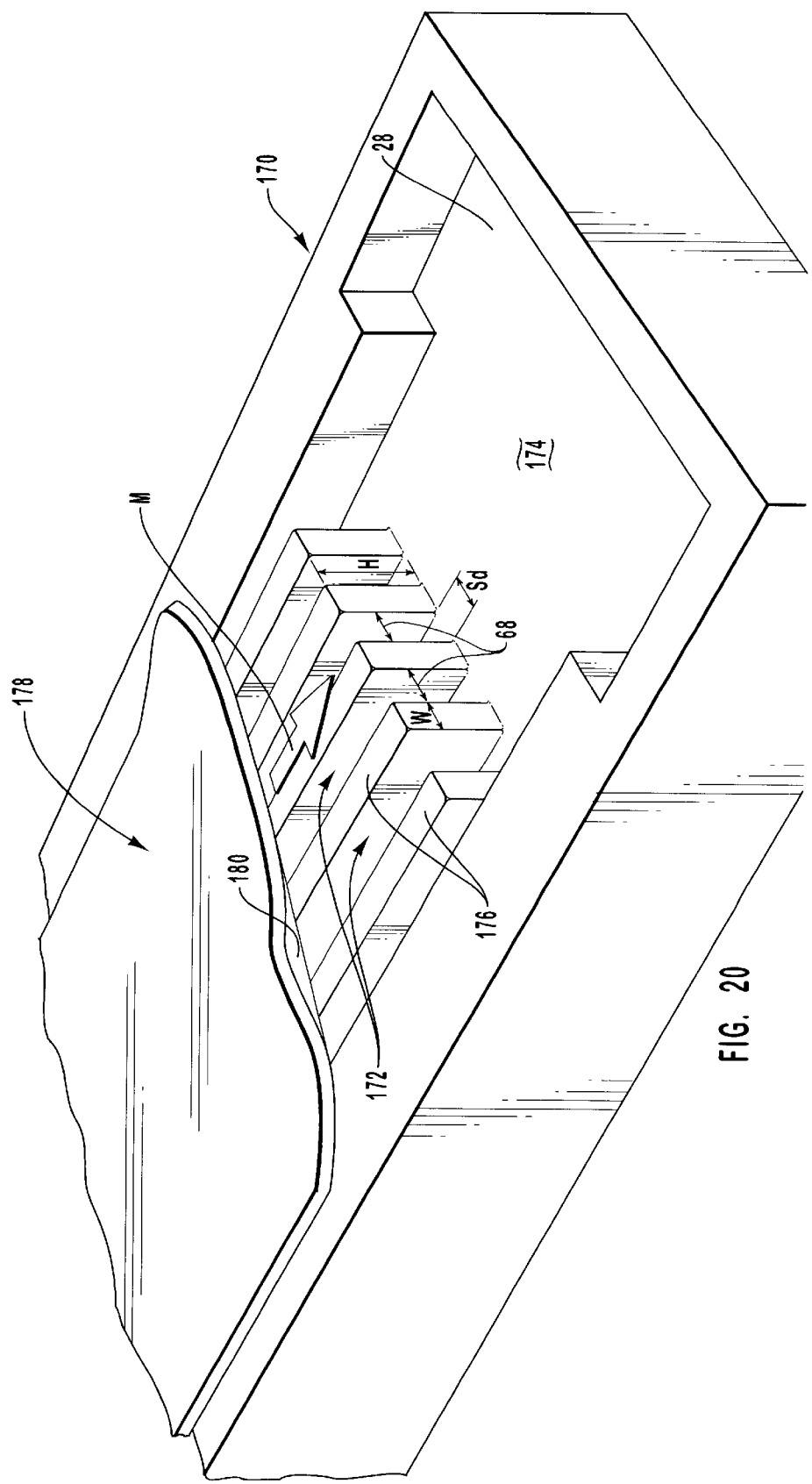
FIG. 20 is a perspective view of a fifth embodiment of an apparatus useful in the processing and study of microstructures and incorporating teachings of the present invention.

FIG. 20 illustrates yet another application of the methods and apparatus of the present invention. There, in the surface of a substrate 170 is formed a set of parallel walls 172 each having a height H and width W. Walls 172 are disposed at a separation distance $S_d$ therebetween, resulting in a series of elongated parallel channels 68. Such structures find use in the processing and study of microstructures, which are typically induced to migrate through channels 68 in migration direction M toward reservoir 174 under positive fluid pressure. Removably sealing the tops 176 of walls 172 and extending between the opposite sides of the array of parallel channels 168 is an elastomeric cover 178. The end 180 of elastomeric cover 178 has been raised upwardly in FIG. 20 to reveal the array of walls 172 therebeneath.

Substrate 170 can be comprised from a rigid material or an elastomeric material, the latter in the manner disclosed herein.

Broadly, the methods disclosed herein relate to reversibly sealing the open side of any microlithographically produced structure in such a manner as the seal may be nondestructibly released. As a result, access can be obtained to the interior of the microlithographically produced structure, and that structure can be cleaned for repeated reuse.

Thus, the present invention allows for the fractionation of microstructures in a reversibly sealable microfabricated structure. In particular, the reversible seal of the present invention allows access to fractionated cells within the structure. The present invention may be embodied in other specific forms without departing from its spirit or essential characteristics. The described embodiments are to be considered in all respects only as illustrative and not restrictive.

What is claimed is:

1. An apparatus for sorting microstructures in a fluid medium, the apparatus comprising:
   a. a receptacle;
   b. one or more structures upstanding from a floor of said receptacle and configured to sort the microstructures as the microstructures flow through said receptacle in said fluid medium; and
   c. a removable cover covering said receptacle and reversibly sealingly engaging ends of said one or more structures, thereby to preclude flow of the microstructures between said cover and said ends of said one or more structures, and thereby selectively to afford access to said receptacle.

2. An apparatus for sorting microstructures in a fluid medium, the apparatus comprising:
   a. a receptacle;
   b. one or more structures upstanding from a floor of said receptacle and configured to sort the microstructures as the microstructures flow through said receptacle in said fluid medium; and
   c. a removable cover covering said receptacle and so engaging ends of said one or more structures as to preclude flow of the microstructures between said cover and said ends of said one or more structures, said cover being hermetically sealed to said receptacle and to said ends of said one or more structures.

3. The apparatus as recited in claim 2, wherein one of said cover and said receptacle is comprised of an elastomer.

4. The apparatus as recited in claim 3, wherein said elastomer is a silicone elastomer.

5. The apparatus, as recited in claim 4, wherein said silicone elastomer comprises polydimethylsiloxame.

6. The apparatus as recited in claim 1, wherein one of said cover and said receptacle is comprised of elastomer and the other of said cover and said receptacle is comprised of any one of silicon, quartz, and sapphire.

7. The apparatus as recited in claim 1, wherein said cover comprises an elastomeric layer carried on a rigid member.

8. The apparatus as recited in claim 3, wherein said receptacle is comprised of an elastomer.

9. The apparatus as recited in claim 8, wherein said receptacle is disposed on a rigid support member.

10. The apparatus as recited in claim 2, wherein said receptacle and said one or more structures are integrally formed of a single material.

11. The apparatus as recited in claim 1, wherein said one or more structures comprise an array of posts upstanding from a floor of said receptacle, each of said posts having a free end remote from said floor of said receptacle, said free end of each of said posts removably engaging said cover.

12. The apparatus as recited in claim 1, wherein said one or more structures comprise an array of elongated bunkers, each of said bunkers having a free end remote from a floor of said receptacle, said free end of each of said bunkers removably engaging said cover.

13. The apparatus as recited in claim 1, wherein said one or more structures comprises an array of elongated walls upstanding from a floor of said receptacle with parallel fluid flow passageways between adjacent of said walls, each of said walls having a top remote from said floor of said receptacle, said top of each of said walls removably engaging said cover.

14. A method of manufacturing an apparatus for sorting microstructures in a fluid medium, the method comprising:
 a. forming a receptacle;
 b. providing within said receptacle one or more structures upstanding from a floor of said receptacle and configured to sort the microstructures as the microstructures flow through said receptacle in said fluid medium;
 c. forming a removeable cover; and
 d. positioning said cover over said receptacle, with said cover reversibly sealingly engaging ends of said one or more structures, thereby to preclude flow of the microstructures between said cover and said ends of said one or more structures, and thereby selectively to afford access to said receptacle.

15. A method of manufacturing an apparatus for sorting microstructures in a fluid medium, the method comprising:
 a. forming a receptacle;
 b. providing within said receptacle one or more structures upstanding from a floor of said receptacle and configured to sort the microstructures as the microstructures flow through said receptacle in said fluid medium;
 c. forming a removeable cover; and
 d. positioning said cover over said receptacle, said cover so engaging ends of said one or more structures as to preclude flow of the microstructures between said cover and said ends of said one or more structures, said cover being removable from said receptacle and hermetically sealed to said receptacle and to said ends of said one or more structures.

16. The method as recited in claim 15, wherein one of said cover and said receptacle is comprised of an elastomer.

17. The method as recited in claim 16, wherein said elastomer is a silicone elastomer.

18. The method as recited in claim 17, wherein said silicone elastomer comprises polydimethylsiloxane.

19. The method as recited in claim 16, wherein the other of said cover and said receptacle is comprised of any one of silicon, quartz, and sapphire.

20. The method as recited in claim 16, wherein said elastomer is cast from a rigid structure.

21. The method as recited in claim 20, wherein said rigid structure is comprised of any one of silicon, quartz, and sapphire.

22. The method as recited in claim 16, wherein said receptacle is comprised of an elastomer.

23. The method as recited in claim 16, wherein said cover is comprised of an elastomer, and said forming of said cover comprises:
 a. depositing a quantity of a liquid elastomer on a rigid member;
 b. spinning said rigid member with said quantity of liquid elastomer thereon, thereby to produce from said quantity of said liquid elastomer a thin layer of said liquid elastomer; and
 c. curing said thin layer of said liquid elastomer, thereby to produce a thin layer of cured elastomer.

24. The method as recited in claim 23, wherein said positioning of said cover comprises disposing said rigid member with said thin layer of cured elastomer over said receptacle and said ends of said one or more structures.

25. The method as recited in claim 23, wherein said forming of said cover further comprises:
 a. cutting a portion of said thin layer of cured elastomer into a predetermined shape; and
 b. removing said predetermined shape of said thin layer of said cured elastomer from said rigid member.

26. The method as recited in claim 16, wherein said cover is comprised of an elastomer, and said forming of said cover comprises:
 a. depositing on a thin flexible sheet a bolus of liquid elastomer;
 b. resting said thin flexible sheet with said bolus of said liquid elastomer thereon on a first rigid surface with said bolus of said elastomer on the side of said thin flexible sheet opposite from said first rigid surface;
 c. compressing said bolus on said thin flexible sheet between said first rigid surface and a second rigid surface, thereby to form said bolus into a thin layer of said liquid elastomer material; and
 d. curing said thin layer of said liquid elastomer, thereby to produce a thin layer of cured elastomer.

27. The method as recited in claim 26, wherein said forming of said cover further comprises:
 a. removing said first rigid surface from adjacent said thin flexible sheet after curing said thin layer; and
 b. peeling said flexible sheet from said thin layer of said cured elastomer.

28. The method as recited in claim 17, wherein a surface of said silicone elastomer is treated to render said surface of said silicone elastomer hydrophilic.

29. The method as recited in claim 22, further comprising treating a surface of said receptacle to render said surface of said receptacle hydrophilic.

30. The method as recited in claim 15, wherein said receptacle and said one or more structures are integrally formed of a single material.

31. The method as recited in claim 14, wherein one of said cover and said receptacle is comprised of an elastomer.

32. The method as recited in claim 14, wherein said receptacle and said one or more structures are integrally formed of a single material.

33. The method as recited in claim 32, wherein said receptacle is comprised of an elastomer.

34. The method as recited in claim 31, wherein said cover is comprised of an elastomer.

35. The apparatus as recited in claim 1, wherein one of said cover and said receptacle is comprised of an elastomer.

36. The apparatus as recited in claim 1, wherein said receptacle and said one or more structures are integrally formed of a single material.

37. The apparatus as recited in claim 36, wherein said receptacle is comprised of an elastomer.

38. The apparatus as recited in claim 35, wherein said cover is comprised of an elastomer.

39. An apparatus for sorting microstructures in a fluid medium, the apparatus comprising:
   a. a receptacle;
   b. one or more structures positioned within said receptacle and configured to sort the microstructures as the microstructures flow through said receptacle in said fluid medium; and
   c. a removable cover covering said receptacle and so engaging ends of said one or more structures as to preclude flow of the microstructures between said cover and said ends of said one or more structures, said cover being comprised of elastomer and being hermetically sealed to said receptacle and to said ends of said one or more structures.

40. The apparatus as recited in claim 39, wherein said elastomer is a silicone elastomer.

41. The apparatus as recited in claim 40, wherein said silicone elastomer comprises polydimethylsiloxane.

42. An apparatus as recited in claim 39, wherein the other of said cover and said substrate is comprised of any one of silicon, quartz, and sapphire.

43. An apparatus for sorting microstructures in a fluid medium, the apparatus comprising:
   a. a receptacle;
   b. one or more structures positioned within said receptacle and configured to sort the microstructures as the microstructures flow through said receptacle in said fluid medium; and
   c. a removable cover comprising an elastomeric layer carried on a rigid member, said removable cover covering said receptacle and reversibly sealingly engaging ends of said one or more structures, thereby to preclude flow of the microstructures between said cover and said ends of said one or more structures, and thereby selectively to afford access to said receptacle.

44. A method of manufacturing an apparatus for sorting microstructures in a fluid medium, the method comprising:
   a. forming a receptacle;
   b. providing within said receptacle one or more structures configured to sort the microstructures as the microstructures flow through said receptacle in said fluid medium;
   c. forming a removable cover; and
   d. positioning said cover over said receptacle, said cover so engaging ends of said one or more structures as to preclude flow of the microstructures between said cover and said ends of said one or more structures, said cover being removable from said receptacle and being hermetically sealed to said receptacle and to said ends of said one or more structures;
   wherein said cover is comprised of an elastomer, and said forming of said cover comprises:
      c(1). depositing a quantity of a liquid elastomer on a rigid member;
      c(2). spinning said rigid member with said quantity of liquid elastomer thereon, thereby to produce from said quantity of said liquid elastomer a thin layer of said liquid elastomer; and
      c(3). curing said thin layer of said liquid elastomer, thereby to produce a thin layer of cured elastomer.

45. The method as recited in claim 44, wherein said elastomer is a silicone elastomer.

46. The method as recited in claim 44, wherein said positioning of said cover comprises disposing said rigid member with said thin layer of cured elastomer over said receptacle and said ends of said one or more structures.

47. The method as recited in claim 44, wherein said forming of said cover further comprises:
   a. cutting a portion of said thin layer of cured elastomer into a predetermined shape; and
   b. removing said predetermined shape of said thin layer of said cured elastomer from said rigid member.

48. A method of manufacturing an apparatus for sorting microstructures in a fluid medium, the method comprising:
   a. forming a receptacle;
   b. providing within said receptacle one or more structures configured to sort the microstructures as the microstructures flow through said receptacle in said fluid medium;
   c. forming a removable cover; and
   d. positioning said cover over said receptacle, said cover so engaging ends of said one or more structures as to preclude flow of the microstructures between said cover and said ends of said one or more structures, said cover being removable from said receptacle and being hermetically sealed to said receptacle and to said ends of said one or more structures;
   wherein said cover is comprised of an elastomer, and said forming of said cover comprises:
      c(1). depositing on a thin flexible sheet a bolus of liquid elastomer;
      c(2). resting said thin flexible sheet with said bolus of said liquid elastomer thereon on a first rigid surface with said bolus of said elastomer on the side of said thin flexible sheet opposite from said first rigid surface;
      c(3). compressing said bolus on said thin flexible sheet between said first rigid surface and a second rigid surface, thereby to form said bolus into a thin layer of said liquid elastomer material; and
      c(4). curing said thin layer of said liquid elastomer, thereby to produce a thin layer of cured elastomer.

49. The method as recited in claim 48, wherein said elastomer is a silicone elastomer.

50. The method as recited in claim 48, wherein said forming of said cover further comprises:
   a. removing said first rigid surface from adjacent said thin flexible sheet after curing said thin layer; and
   b. peeling said flexible sheet from said thin layer of said cured elastomer.

51. A method of manufacturing an apparatus for sorting microstructures in a fluid medium, the method comprising:
   a. forming a receptacle;
   b. providing within said receptacle one or more structures configured to sort the microstructures as the microstructures flow through said receptacle in said fluid medium;
   c. forming a removable cover; and
   d. positioning said cover over said receptacle, said cover so engaging ends of said one or more structures as to preclude flow of the microstructures between said cover and said ends of said one or more structures, said cover being removable from said receptacle and being hermetically sealed to said receptacle and to said ends of said one or more structures;
   wherein said cover is comprised of an elastomer and a surface of said elastomer is treated to render said surface hydrophilic.

52. The method as recited in claim 51, wherein said elastomer is a silicone elastomer.

53. A method of manufacturing an apparatus for sorting microstructures in a fluid medium, the method comprising:

a. forming a receptacle;

b. providing within said receptacle one or more structures configured to sort the microstructures as the microstructures flow through said receptacle in said fluid medium;

c. forming a removable cover; and d. positioning said cover over said receptacle, said cover so engaging ends of said one or more structures as to preclude flow of the microstructures between said cover and said ends of said one or more structures, said cover being removable from said receptacle and being hermetically sealed to said receptacle and to said ends of said one or more structures; wherein said receptacle is comprised of an elastomer and said method further comprises treating a surface of said receptacle to render said surface hydrophilic.

54. An apparatus for sorting microstructures, the apparatus comprising:

a. a microlithographically produced sorting structure; and b. a cover sealingly positioned against an open side of said sorting structure and nondestructively removable therefrom, said cover being comprised of an elastomer.

55. An apparatus for sorting microstructures in a fluid medium, the apparatus comprising:

a. a receptacle;

b. one or more structures positioned within said receptacle and configured to sort the microstructures as the microstructures flow through said receptacle in said fluid medium; and c. a removable cover covering said receptacle and reversibly sealingly engaging ends of said one or more structures, thereby to preclude flow of the microstructures between said cover and said ends of said one or more structures, and thereby selectively to afford access to said receptacle, said cover being comprised of an elastomer.

56. An apparatus for sorting microstructures in a fluid medium, the apparatus comprising:

a. a receptacle;

b. one or more structures within said receptacle and configured to sort the microstructures as the microstructures flow through said receptacle in said fluid medium; and c. a cover comprised of an elastomer, said cover covering said receptacle and being sealingly engaged with ends of said one or more structures.

57. The apparatus as recited in claim 56, wherein said receptacle is comprised of an elastomer.

58. The apparatus as recited in claim 56, wherein a plurality of said sorting structures are within said receptacle.

59. The apparatus as recited in claim 58, wherein said plurality of structures are arranged in an array.

60. The apparatus as recited in claim 58, wherein said plurality of structures are formed on a floor of said receptacle.

\* \* \* \* \*